United States Patent
Ben-Ami et al.

(10) Patent No.: US 12,288,417 B2
(45) Date of Patent: *Apr. 29, 2025

(54) OBTAINING HIGH-RESOLUTION OCULOMETRIC PARAMETERS

(71) Applicant: NeuraLight Ltd., Tel Aviv (IL)

(72) Inventors: Edmund Ben-Ami, Tel Aviv (IL);
Micha Yochanan Breakstone, Austin, TX (US); Rotem Zvi Bar-Or, Boulder, CO (US); Vladimir Anisimov, Tel-Aviv (IL)

(73) Assignee: NeuraLight, Ltd., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/824,578

(22) Filed: Sep. 4, 2024

(65) Prior Publication Data

US 2024/0428618 A1     Dec. 26, 2024

Related U.S. Application Data

(63) Continuation of application No. 17/722,095, filed on Apr. 15, 2022, now Pat. No. 12,118,825.
(Continued)

(51) Int. Cl.
*G06N 3/04*     (2023.01)
*A61B 3/00*     (2006.01)
(Continued)

(52) U.S. Cl.
CPC ............ *G06V 40/18* (2022.01); *A61B 3/0025* (2013.01); *A61B 3/113* (2013.01); *A61B 5/163* (2017.08);
(Continued)

(58) Field of Classification Search
None
See application file for complete search history.

(56) References Cited

U.S. PATENT DOCUMENTS

| 6,820,979 B1 | 11/2004 | Stark et al. |
| 7,428,320 B2 | 9/2008 | Northcott et al. |

(Continued)

FOREIGN PATENT DOCUMENTS

| CA | 2618352 A1 | 2/2007 |
| CN | 106265006 A | 1/2017 |

(Continued)

OTHER PUBLICATIONS

Qidwai, U., and Qidwai, U., "Blind Deconvolution for Retinal Image Enhancement," IEEE EMBS Conference on Biomedical Engineering and Sciences pp. 20-25, (2010).
(Continued)

*Primary Examiner* — Mohammed Rachedine
(74) *Attorney, Agent, or Firm* — Sterne, Kessler, Goldstein & Fox P.L.L.C.

(57) ABSTRACT

Disclosed are systems and methods for extracting high resolution oculometric parameters. A video stream having a video of a face of a user is processed to obtain a set of oculometric parameters, such as eyelid data, iris data (e.g., iris translation, iris radius and iris rotation), and pupil data (e.g., pupil center and pupil radius) at a first resolution. A deconvolution process is performed on the video stream to improve accuracy or resolution of the oculometric parameters, based on stimulus information of a video stimulus displayed on a client device associated with the user, environment data of an environment in which the user is located, device data of the client device, etc. The oculometric parameters are then processed using a prediction model that is trained based on high resolution oculometric parameters obtained using eye tracking devices to predict oculometric parameters at a resolution greater than the first resolution.

20 Claims, 7 Drawing Sheets

Related U.S. Application Data

(60) Provisional application No. 63/183,388, filed on May 3, 2021.

(51) Int. Cl.

| | | |
|---|---|---|
| *A61B 3/113* | (2006.01) | |
| *A61B 5/16* | (2006.01) | |
| *G06F 3/01* | (2006.01) | |
| *G06N 3/084* | (2023.01) | |
| *G06N 3/09* | (2023.01) | |
| *G06T 7/00* | (2017.01) | |
| *G06T 7/246* | (2017.01) | |
| *G06V 10/82* | (2022.01) | |
| *G06V 40/18* | (2022.01) | |

(52) U.S. Cl.
CPC ............ *G06F 3/013* (2013.01); *G06T 7/0012* (2013.01); *G06T 2207/20081* (2013.01); *G06T 2207/30041* (2013.01)

(56) References Cited

U.S. PATENT DOCUMENTS

| | | | |
|---|---|---|---|
| 7,753,525 B2 | 7/2010 | Hara et al. | |
| 7,869,627 B2 | 1/2011 | Northcott et al. | |
| 8,061,840 B2 | 11/2011 | Mizuochi | |
| 8,132,916 B2 | 3/2012 | Johansson | |
| 9,965,860 B2 | 5/2018 | Nguyen et al. | |
| 10,016,130 B2 | 7/2018 | Ganesan et al. | |
| 10,039,445 B1* | 8/2018 | Torch | A61B 5/18 |
| 10,109,056 B2 | 10/2018 | Nguyen et al. | |
| 10,231,614 B2 | 3/2019 | Krueger | |
| 10,575,728 B2 | 3/2020 | Zakariaie et al. | |
| 10,620,700 B2 | 4/2020 | Publicover et al. | |
| 10,713,813 B2 | 7/2020 | De Villers-Sidani et al. | |
| 10,713,813 B2 | 7/2020 | De Villers-Sidani et al. | |
| 10,742,944 B1* | 8/2020 | Abou Shousha | A61B 3/085 |
| 11,074,714 B2 | 7/2021 | De Villers-Sidani et al. | |
| 11,382,545 B2 | 7/2022 | Zakariaie et al. | |
| 11,503,998 B1 | 11/2022 | De Villers-Sidani et al. | |
| 11,513,593 B2 | 11/2022 | Drozdov et al. | |
| 11,514,720 B2 | 11/2022 | Haimovitch-Yogev et al. | |
| 11,556,741 B2* | 1/2023 | Dierkes | G06V 10/772 |
| 11,776,315 B2 | 10/2023 | Haimovitch-Yogev et al. | |
| 12,033,432 B2 | 7/2024 | Ben-Ami et al. | |
| 2005/0228236 A1 | 10/2005 | Diederich et al. | |
| 2007/0009169 A1 | 1/2007 | Bhattacharjya | |
| 2009/0018419 A1 | 1/2009 | Torch | |
| 2014/0171756 A1 | 6/2014 | Waldorf et al. | |
| 2014/0320397 A1 | 10/2014 | Hennessey et al. | |
| 2014/0364761 A1 | 12/2014 | Benson et al. | |
| 2015/0077543 A1 | 3/2015 | Kerr et al. | |
| 2015/0293588 A1 | 10/2015 | Strupczewski et al. | |
| 2016/0150955 A1 | 6/2016 | Kiderman et al. | |
| 2017/0135577 A1 | 5/2017 | Komogortsev | |
| 2017/0151089 A1 | 6/2017 | Chernyak | |
| 2017/0231490 A1 | 8/2017 | Toth et al. | |
| 2017/0249434 A1 | 8/2017 | Brunner | |
| 2017/0364732 A1 | 12/2017 | Komogortsev | |
| 2018/0018515 A1 | 1/2018 | Spizhevoy et al. | |
| 2018/0249941 A1* | 9/2018 | Liston | A61B 3/0041 |
| 2019/0246969 A1 | 8/2019 | Thomas et al. | |
| 2019/0343382 A1 | 11/2019 | Rubner et al. | |
| 2020/0268296 A1 | 8/2020 | Alcaide et al. | |
| 2020/0305708 A1 | 10/2020 | Krueger | |
| 2020/0323480 A1 | 10/2020 | Shaked et al. | |
| 2020/0405148 A1 | 12/2020 | Tran | |
| 2021/0174959 A1 | 6/2021 | Abel Fernandez | |
| 2021/0186318 A1 | 6/2021 | Yellin et al. | |
| 2021/0186395 A1 | 6/2021 | Zakariaie et al. | |
| 2021/0186397 A1 | 6/2021 | Weisberg et al. | |
| 2021/0228142 A1 | 7/2021 | Sheehy et al. | |
| 2021/0248720 A1 | 8/2021 | Ziesche et al. | |
| 2021/0327595 A1 | 10/2021 | Abdallah | |
| 2022/0019791 A1 | 1/2022 | Drozdov et al. | |
| 2022/0206571 A1 | 6/2022 | Drozdov et al. | |
| 2022/0211310 A1 | 7/2022 | Zakariaie et al. | |
| 2022/0236797 A1 | 7/2022 | Drozdov et al. | |
| 2022/0301294 A1 | 9/2022 | Boutinon | |
| 2022/0313083 A1 | 10/2022 | Zakariaie et al. | |
| 2022/0351545 A1* | 11/2022 | Ben-Ami | A61B 3/113 |
| 2022/0354363 A1 | 11/2022 | Ben-Ami et al. | |
| 2022/0390771 A1 | 12/2022 | David et al. | |
| 2023/0074569 A1 | 3/2023 | Drozdov et al. | |
| 2023/0233072 A1 | 7/2023 | Haimovitch-Yogev et al. | |
| 2023/0334326 A1 | 10/2023 | Haimovitch-Yogev et al. | |
| 2024/0037987 A1 | 2/2024 | Ben-Ami et al. | |
| 2024/0119594 A1 | 4/2024 | Ben-Ami et al. | |

FOREIGN PATENT DOCUMENTS

| | | | | |
|---|---|---|---|---|
| EP | 1947604 A1 | 7/2008 | | |
| EP | 3140780 B1 * | 11/2020 | ......... | G02B 27/0093 |
| WO | WO-2020110121 A1 * | 6/2020 | ............ | A61B 3/113 |
| WO | WO-2020190648 A1 * | 9/2020 | ........... | A61B 3/0008 |
| WO | WO-2020235939 A2 | 11/2020 | | |
| WO | WO-2021097300 A1 | 5/2021 | | |

OTHER PUBLICATIONS

Torres-Salomao, L.A., et al., "Pupil Diameter Size Marker for Incremental Mental Stress Detection," International Conference on E-Health Networking, Application & Services pp. 286-291, (2015).

Akinyelu, A.A. and Blignaut, P., "Convolutional Neural Network-Based Technique for Gaze Estimation on Mobile Devices," Frontiers in Artificial Intelligence 4:796825 11 pages, Frontiers Media SA, Switzerland (Jan. 2022).

Ali, E.N., et al., "Pupillary Response to Sparse Multifocal Stimuli in Multiple Sclerosis Patients," Multiple Sclerosis Journal 20(7):854-861, SAGE Publications, United Kingdom (Nov. 2013).

Aljaafreh, A., et al., "A Low-cost Webcam-based Eye Tracker and Saccade Measurement System," International Journal of Circuits, Systems and Signal Processing 14:102-107, (Apr. 2020).

Alnajar, F., et al., "Auto-Calibrated Gaze Estimation Using Human Gaze Patterns," International Journal of Computer Vision 124:223-236, (2017).

Bafna, T., et al., "EyeTell: Tablet-based Calibration-free Eye-typing Using Smooth-pursuit Movements," Proceedings of the ETRA '21 Short Papers, (2021).

Bedell, H.E., et al., "Eye Movement Testing in Clinical Examination," Vision Research 90:32- 37, Elsevier Science Limited, United Kingdom (Sep. 2013).

Bijvank, J.A.N., et al., "Quantification of Visual Fixation in Multiple Sclerosis," Investigative Ophthalmology & Visual Science 60(5): 1372-1383, Association for Research in Vision and Ophthalmology (Arvo), United States (Apr. 2019).

Borza, D., et al., "Real-Time Detection and Measurement of Eye Features from Color Images," Sensors 16(7):1105 1-24, MDPI, Switzerland (Jul. 2016).

Chen, S. and Epps, J., "Eyelid and Pupil Landmark Detection and Blink Estimation Based on Deformable Shape Models for Near-Field Infrared Video," Frontiers in ICT 6:18 1-11, (Oct. 2019).

Cherng, Y., et al., "Background Luminance Effects on Pupil Size Associated With Emotion and Saccade Preparation," Scientific Reports 10(1):15718 11 Pages, Nature Publishing Group, United Kingdom (Sep. 2020).

Chernov, N., et al., "Fitting Quadratic Curves to Data Points," British Journal of Mathematics & Computer Science 4(1):33-60, (2014).

De Almeida Junior, F.L., et al., "Image Quality Treatment to Improve Iris Biometric Systems," Infocomp Journal of Computer Science 16(1-2):21-30, (2017).

De Seze, J., et al., "Pupillary Disturbances in Multiple Sclerosis: Correlation With MRI Findings," Journal of the Neurological Sciences 188(1-2):37-41, Elsevier, Netherlands (Jul. 2001).

De Villers-Sidani, E., et al., "A Novel Tablet-based Software for the Acquisition and Analysis of Gaze and Eye Movement Parameters: A Preliminary Validation Study in Parkinson's Disease," Frontiers

(56) References Cited

OTHER PUBLICATIONS in Neurology 14(1204733):1-10, Frontiers Research Foundation, Switzerland (Jun. 2023).
De Villers-Sidani, E., et al., "Oculomotor Analysis to Assess Brain Health: Preliminary Findings From a Longitudinal Study of Multiple Sclerosis Using Novel Tablet-based Eye-tracking Software," Frontiers in Neurology 14(1243594):1-11, Frontiers Research Foundation, Switzerland (Sep. 2023).
Derwenskus, J., et al., "Abnormal Eye Movements Predict Disability in MS: Two-year Follow-up," Annals of the New York Academy of Sciences 1039:521-523, Blackwell, United States (Apr. 2005).
Felmingham, K., "Eye Tracking and PTSD," Comprehensive Guide to Post-traumatic Stress Disorder Chapter 69:1241-1256, (Jan. 2015).
Ferreira, M., et al., "Using Endogenous Saccades to Characterize Fatigue in Multiple Sclerosis," Multiple Sclerosis and Related Disorders 14:16-22, Elsevier B. V., Netherlands (May 2017).
Fielding, J., et al., "Ocular Motor Signatures of Cognitive Dysfunction in Multiple Sclerosis," Nature Reviews. Neurology, 11(11):637-645, Nature Publishing Group, United Kingdom (Nov. 2015).
Fink, L., et al., "From Pre-processing to Advanced Dynamic Modeling of Pupil Data," Behavior Research Methods 56(3):1376-1412, Springer, United States (Jun. 2023).
Frohman, E.M., et al., "Quantitative Oculographic Characterisation of Internuclear Ophthalmoparesis in Multiple Sclerosis: The Versional Dysconjugacy Index Z Score," Journal of Neurology, Neurosurgery, and Psychiatry 73(1):51-55, BMJ Publishing Group, United Kingdom (Jul. 2002).
Frohman, E.M., et al., "The Neuro-Ophthalmology of Multiple Sclerosis", The Lancet Neurology, 4(2):111-121, Lancet Public Group, United Kingdom (Feb. 2005).
Frohman, T.C., et al., "Accuracy of Clinical Detection of INO in MS: Corroboration With Quantitative Infrared Oculography," Neurology 61(6):848-850, Lippincott Williams & Wilkins, United States (Sep. 2003).
Grillini, A., et al., "Eye Movement Evaluation in Multiple Sclerosis and Parkinson's Disease Using a Standardized Oculomotor and Neuro-Ophthalmic Disorder Assessment (SONDA)," Frontiers in Neurology 11:971 1-15, Frontiers Research Foundation, Switzerland (Sep. 2020).
Guri, M., et al., "BRIGHTNESS: Leaking Sensitive Data from Air-Gapped Workstations via Screen Brightness," IEEE 12th CMI Conference on Cybersecurity and Privacy 7 pages, (2020).
Hasasneh, A., et al., "Deep Learning Approach for Automatic Classification of Ocular and Cardiac Artifacts in Meg Data," Hindawi Journal of Engineering, 1-10, (Apr. 2018).
Hoffner, S., et al., "Gaze Tracking Using Common Webcams," Osnabruck University, 89 pages (Feb. 2018).
Holzman, P.S., et al., "Eye-tracking Dysfunctions in Schizophrenic Patients and Their Relatives," Archives of General Psychiatry 31(2):143-151, American Medical Association, United States (Aug. 1974).
Hooge, I.T.C., et al., "Gaze Tracking Accuracy in Humans: One Eye is Sometimes Better Than Two," Behavior Research Methods 51(6):2712-2721, Springer, United States (Dec. 2019).
Hou, L., et al., "Illumination-Based Synchronization of High-Speed Vision Sensors," Sensors 10(6):5530-5547, Basel, Switzerland (2010).
Hutt, S. and D'Mello, S.K., "Evaluating Calibration-free Webcam-based Eye Tracking for Gaze-based User Modeling," ICMI '22: Proceedings of the 2022 International Conference on Multimodal Interaction 224-235, (Nov. 2022).
International Search Report and Written Opinion for Application No. PCT/US2022/027201, mailed on Sep. 19, 2022, 10 pages.
International Search Report and Written Opinion for Application No. PCT/US2022/027312, mailed on Oct. 27, 2022, 10 pages.
Jacobsen, J., "Pupillary Function in Multiple Sclerosis," Acta Neurologica Scandinavica 82(6):392-395, Wiley-Blackwell, Denmark (Dec. 1990).
Jamaludin, S., et al., "Deblurring of Noisy Iris Images in Iris Recognition," Bulletin of Electrical Engineering and Informatics (BEEI) 10(1):156-159, (Feb. 2021).
Joyce, D.S., et al., "Melanopsin-mediated Pupil Function is Impaired in Parkinson's Disease," Scientific Reports 8(1):7796, Nature Publishing Group, United Kingdom (May 2018).
Kelbsch, C., et al., "Standards in Pupillography," Frontiers in Neurology 10(129):1-26, Frontiers Research Foundation, Switzerland (Feb. 2019).
Krafka, K., et al., "Eye Tracking for Everyone," The IEEE Conference on Computer Vision and Pattern Recognition (CVPR) 2176-2184, (Jun. 2016).
Lai, H., et al., "Measuring Saccade Latency Using Smartphone Cameras," IEEE Journal of Biomedical and Health Informatics 24(3):885-897, Institute of Electrical and Electronics Engineers, United States (Mar. 2020).
Liu, G., et al., "A Differential Approach for Gaze Estimation," IEEE Transactions on Pattern Analysis and Machine Intelligence 43(3):1092-1099, IEEE Computer Society, United States (Mar. 2021).
Liu, J., et al., "Iris Image Deblurring Based on Refinement of Point Spread Function," Chinese Conference on Biometric Recognition (CCBR), Lecture Notes in Computer Science 7701:184-192, (Dec. 2012).
Lizak, N., et al., "Impairment of Smooth Pursuit as a Marker of Early Multiple Sclerosis," Frontiers in Neurology 7(3):206 1-7, Frontiers Research Foundation, Switzerland (Nov. 2016).
Mahanama, B., et al., "Eye Movement and Pupil Measures: A Review," Frontiers in Computer Science 3:733531 1-12, (Jan. 2022).
Matza, L.S., "Multiple Sclerosis Relapse: Qualitative Findings From Clinician and Patient Interviews," Multiple Sclerosis and Related Disorders 27 Pages, Elsevier B. V., Netherlands (Jan. 2019).
Model, D., "A Calibration Free Estimation of the Point of Gaze and Objective Measurement of Ocular Alignment in Adults and Infants," University of Toronto 160 pages, (2011).
Mollers, Maximilian., "Calibration-Free Gaze Tracking an Experimental Analysis," RWTH Aachen University 111 pages, (2007).
Niestroy, A., "Neuro-ophthalmologic Aspects of Multiple Sclerosis: Using Eye Movements as a Clinical and Experimental Tool," Clinical Ophthalmology 1(3):267-272, Dove Medical Press, New Zealand (Sep. 2007).
Park, S., et al., "Few-Shot Adaptive Gaze Estimation," Proceedings of the IEEE/CVF International Conference on Computer Vision (ICCV), 13 pages, (2019).
Patel, A.S., et al., "Optical Axes and Angle Kappa," American Academy of Ophthalmology, (Oct. 2021).
Peysakhovich, V., et al., "The Impact of Luminance on Tonic and Phasic Pupillary Responses to Sustained Cognitive Load," International Journal of Psychophysiology 112:40-45, Elsevier, Netherlands (Feb. 2017).
Pfeuffer, K., et al., "Pursuit Calibration: Making Gaze Calibration Less Tedious and More Flexible," UIST 13 Proceedings of the 26th Annual Acm Symposium on User Interface Software and Technology 261-270, (Oct. 2013).
Pi, J. and Shi, B.E., et al., "Task-embedded Online Eye-tracker Calibration for Improving Robustness to Head Motion," Proceedings of the 11th ACM Symposium on Eye Tracking Research & Applications ETRA '19 8:1-9, (Jun. 2019).
Polak, P.E., et al., "Locus Coeruleus Damage and Noradrenaline Reductions in Multiple Sclerosis and Experimental Autoimmune Encephalomyelitis," Brain 134(Pt 3):665-677, Oxford University Press, United Kingdom (Mar. 2011).
Rasulo, F.A., et al., "Essential Noninvasive Multimodality Neuromonitoring for the Critically Ill Patient," Critical Care 24(1):100 12 Pages, BioMed Central Ltd, United Kingdom (Mar. 2020).
Rayner, K., "Eye Movements in Reading and Information Processing: 20 Years of Research," Psychological Bulletin 124(3):372-422, American Psychological Association, United States (Nov. 1998).
Rodrigues, A.C., "Response Surface Analysis: A Tutorial for Examining Linear and Curvilinear Effects," Journal of Contemporary Administration 25(6):1-14, (Apr. 2021).

(56) References Cited

OTHER PUBLICATIONS

Romero, K., et al., "Neurologists' Accuracy in Predicting Cognitive Impairment in Multiple Sclerosis," Multiple Sclerosis and Related Disorders 4(4):291-295, Elsevier B. V., Netherlands (Jul. 2015).

Schuler, C.J., "Machine Learning Approaches to Image Deconvolution," Dissertation University of Tubingen, 1-142, Germany (2017).

Schweitzer, R and Rolfs, M., "An Adaptive Algorithm for Fast and Reliable Online Saccade Detection," Behavior Research Methods 52(3):1122-1139, Springer, United States (Jun. 2020).

Serra, A., et al., "Eye Movement Abnormalities in Multiple Sclerosis: Pathogenesis, Modeling, and Treatment," Frontiers in Neurology 9(31):1-7, Frontiers Research Foundation, Switzerland (Feb. 2018).

Serra, A., et al., "Role of Eye Movement Examination and Subjective Visual Vertical in Clinical Evaluation of Multiple Sclerosis," Journal of Neurology 250(5):569-575, Springer-Verlag, Germany (May 2003).

Servillo, G., et al., "Bedside Tested Ocular Motor Disorders in Multiple Sclerosis Patients," Multiple Sclerosis International 2014:732329 1-5, Hindawi Publishing Corporation, Egypt (Apr. 2014).

Sheehy, C.K., et al., "Fixational Microsaccades: A Quantitative and Objective Measure of Disability in Multiple Sclerosis," Multiple Sclerosis 26(3):343-353, SAGE Publications, United Kingdom (Mar. 2020).

Smith, J.D., "Viewpointer: Lightweight Calibration-free Eye Tracking for Ubiquitous Handsfree Deixis," UIST 05: Proceedings of the 18th Annual ACM Symposium on User Interface Software and Technology, 84 pages (2005).

Strobl, M.A.R., et al., "Look Me in the Eye: Evaluating the Accuracy of Smartphone-based Eye Tracking for Potential Application in Autism Spectrum Disorder Research," Biomedical Engineering Online 18(1):51 1-12, BioMed Central, United Kingdom (May 2019).

System and Method for Measuring Delay from Monitor Output to Camera Sensor, Unpublished Disclosure; 16 pages.

Teikari, P., et al., "Embedded Deep Learning in Ophthalmology: Making Ophthalmic Imaging Smarter," Therapeutic Advances in Ophthalmology, 1-21, Sage Publications Limited, United States (Mar. 2019).

Tur, C., et al., "Assessing Treatment Outcomes in Multiple Sclerosis Trials and in the Clinical Setting," Nature Reviews. Neurology 14(2):164 Pages, Nature Publishing Group, United Kingdom (Feb. 2018).

Valliappan, N., et al., "Accelerating Eye Movement Research via Accurate and Affordable Smartphone Eye Tracking," Nature Communications 11(1):4553 1-12, Nature Publishing Group, United Kingdom (Sep. 2020).

Valliappan, N., et al., "Accelerating Eye Movement Research via Accurate and Affordable Smartphone Eye Tracking," Nature Communications 11(1):4553 1-18, Nature Publishing Group, United Kingdom (Jul. 2020).

Van Munster, C.E.P., et al., "Outcome Measures in Clinical Trials for Multiple Sclerosis," CNS Drugs 31(3):217-236, Springer International, New Zealand (Mar. 2017).

Wang, K. and Ji, Q., "3D Gaze Estimation without Explicit Personal Calibration," Pattern Recognition 79:216-227, Elsevier, (Jul. 2018).

Williams, B.M., et al., "Fast Blur Detection and Parametric Deconvolution of Retinal Fundus Images," Fetal, Infan and Ophthalmic Medical Image Analysis, 1-8, Springer, Cham (2017).

Yang, T., et al., "Gaze Angle Estimate and Correction in Iris Recognition," IEEE Symposium on Computational Intelligence in Biometrics and Identity Management (CIBIM) 7 Pages, (Dec. 2014).

Zammarchi, G., et al., "Application of Eye Tracking Technology in Medicine: A Bibliometric Analysis," Vision 5(4):56 1-14, MDPI AG, Switzerland (Nov. 2021).

Zhang, Y., et al., "Luminance Effects on Pupil Dilation in Speech-in-noise Recognition," PLoS One 17(12):e0278506 1-18, Public Library of Science, United States (Dec. 2022).

Extended European Search Report directed to European Patent Application No. 22799372.2, mailed Feb. 17, 2025; 8 pages.

* cited by examiner

OBTAINING HIGH-RESOLUTION OCULOMETRIC PARAMETERS

CROSS REFERENCE TO RELATED PATENT APPLICATIONS

This patent application is a continuation of U.S. patent application Ser. No. 17/722,095, entitled "OBTAINING HIGH-RESOLUTION OCULOMETRIC PARAMETERS," filed Apr. 15, 2022, which claims the benefit of U.S. Provisional Patent Application No. 63/183,388, entitled "MEASURING HIGH RESOLUTION EYE MOVEMENTS USING BLIND DECONVOLUTION TECHNIQUES," filed on May 3, 2021, which are incorporated by reference herein in their entireties.

BACKGROUND

Several papers have been published which demonstrate the connections between minute eye movements and the progression of neurological disorders (see, for example, References section below). Typically, these eye movements are measured in well-controlled lab settings (e.g., no movements, controlled ambient light, or other such parameters) using dedicated devices (e.g., infrared eye trackers, pupilometers, or other such devices), which is a challenge to set up, cost prohibitive, or may involve a significant amount of time and effort to create or maintain the controlled setup. Some prior technologies use neural networks to obtain these eye movements but do not attain the needed resolution for measurements (e.g., around 0.1 mm or greater resolution). Additionally, prior technologies focus on measuring reactions of the eye to specific standardized stimuli (e.g., controlled light stimulus, stimulus provided to measure specific parameters, stimulus that a patient needs to me made aware of, or other such stimulus) with controlled ambient conditions. These and other drawbacks exist.

SUMMARY

Disclosed embodiments relate to systems and methods for facilitating measurement of minute eye parameters or movements with video captured by standard cameras (e.g., smartphone camera, webcam, or another video capturing device) and without the need for controlled settings. The embodiments obtain various high resolution oculometric parameters. For example, the embodiments may obtain eyelid data, such as coordinates of eyelid boundaries. In another example, the embodiments obtain iris data such as iris translation or iris center, iris rotation, iris radius, iris visible fraction, or iris coverage asymmetry. In yet another example, the embodiments obtain pupil data such as a pupil center, a pupil radius, a pupil visible fraction, or a pupil coverage asymmetry. The oculometric parameters are obtained at a high resolution, for example, at a sub-pixel level, 0.1 mm, or other higher resolution. In some embodiments, the oculometric parameters may be used in determining eye movement measurements, such as pupillary response parameter, gaze, saccade, fixation, etc., which may be used to produce digital biomarkers that may further be used to diagnose or measure progress of a neurological condition or disorder. The digital biomarkers are objective, sensitive, accurate, correlated with disease progression, and may be conducted remotely and even in a distributed manner. The oculometric parameters or eye movement parameters may be obtained using non-standard stimulus presented to the user on a user device (e.g., stimulus that a patient need not be made aware of, stimulus that may be used to measure multiple parameters, stimulus such as a video playing on a display device being observed by the user, or other such stimulus that does not need controlled ambient lighting conditions).

In some embodiments, the disclosed embodiments may use probabilistic methods (e.g., maximum likelihood estimate, or other such method) or signal processing methods (e.g., blind deconvolutions, or other such method) to increase resolution and ascertain oculometric parameters, eye movement parameters at a very high resolution (e.g., at a sub-pixel level, 0.1 mm, or other higher resolution) on layers of data present in video frame sequences of eye movements captured by standard cameras in uncontrolled settings. The disclosed embodiments may employ prediction models (e.g., machine learning (ML) models such as neural networks) to obtain one or more oculometric parameters at high resolution.

Various other aspects, features, and advantages of the inventions will be apparent through the detailed description of the invention and the drawings attached hereto. It is also to be understood that both the foregoing general description and the following detailed description are exemplary and not restrictive of the scope of the inventions. As used in the specification and in the claims, the singular forms of "a", "an", and "the" include plural referents unless the context clearly dictates otherwise. In addition, as used in the specification and the claims, the term "or" means "and/or" unless the context clearly dictates otherwise.

DETAILED DESCRIPTION

In the following description, for the purposes of explanation, numerous specific details are set forth in order to provide a thorough understanding of the embodiments of the invention. It will be appreciated, however, by those having skill in the art that the embodiments of the invention may be practiced without these specific details or with an equivalent arrangement. In other cases, well-known structures and devices are shown in block diagram form in order to avoid unnecessarily obscuring the embodiments of the invention.

Figure 1A:
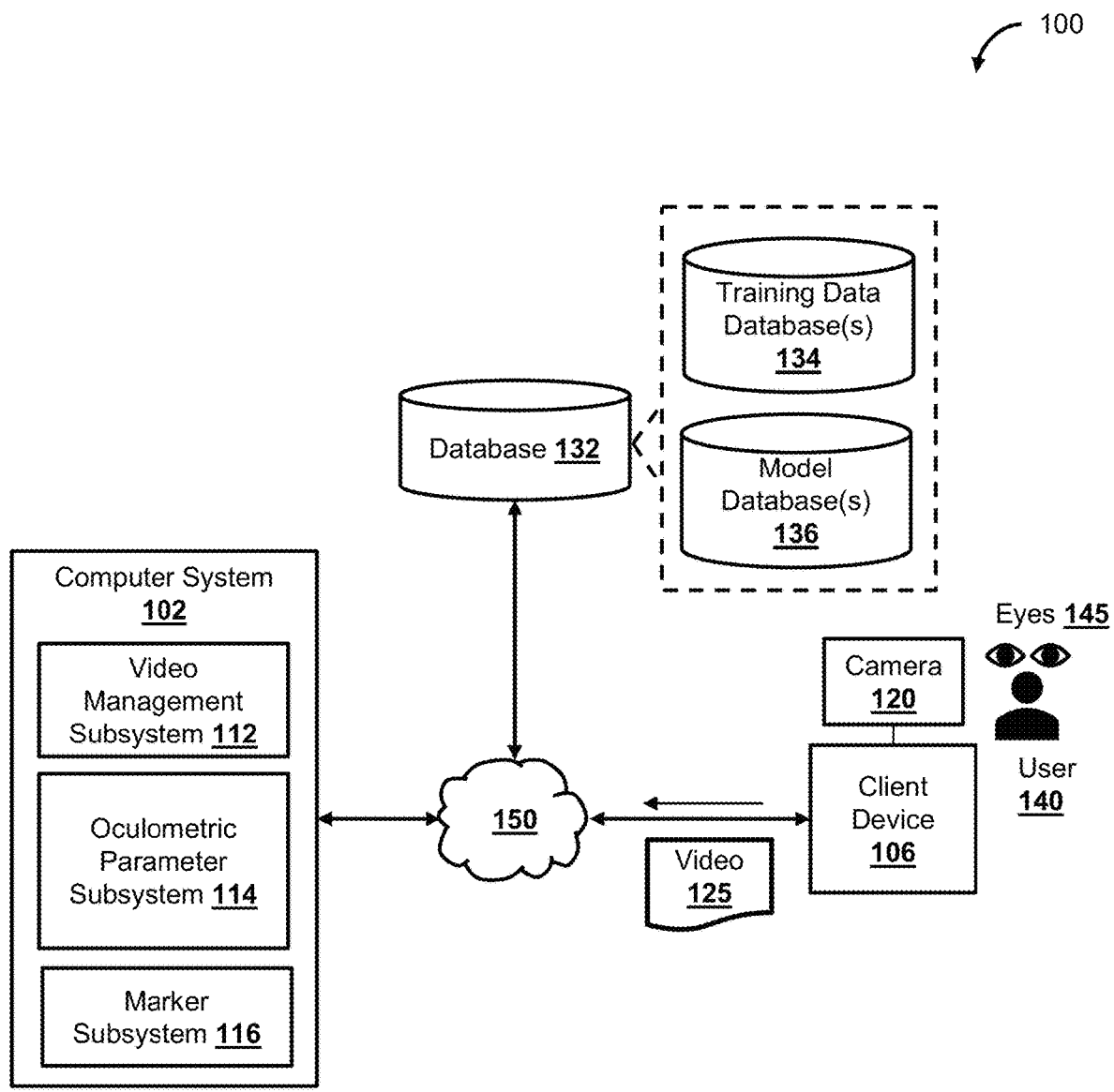
FIG. 1A shows a system for facilitating measurement of oculometric parameters and eye movements of a user, consistent with various embodiments.
Figure 1B:
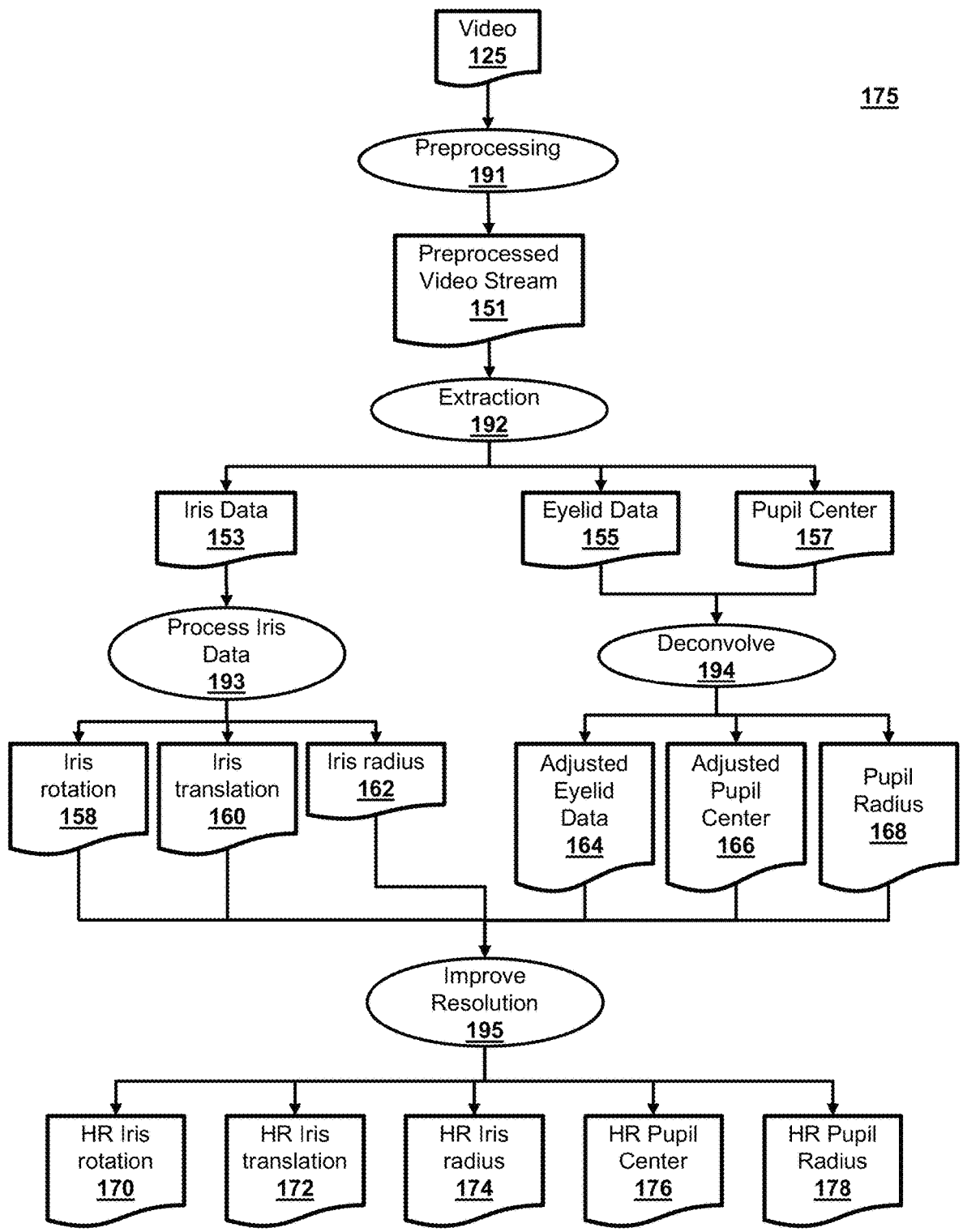
FIG. 1B shows a process of extracting high resolution (HR) oculometric parameters associated with an eye, consistent with various embodiments.

FIG. 1A shows a system 100 for facilitating measurement of oculometric parameters and eye movements of a user, consistent with various embodiments. FIG. 1B shows a process 175 of extracting high resolution (HR) oculometric parameters associated with an eye, consistent with various embodiments. As shown in FIG. 1A, system 100 may include computer system 102, client device 106, or other components. By the way of example, computer system 102 may include any computing device, such as a server, a personal computer (PC), a laptop computer, a tablet computer, a hand-held computer, or other computer equipment. Computer system 102 may include video management subsystem 112, oculometric parameter subsystem (OPS) 114, marker subsystem 116, or other components. The client device 106 may include any type of mobile terminal, fixed terminal, or other device. By way of example, client device 106 may include a desktop computer, a notebook computer, a tablet computer, a smartphone, a wearable device, or other client device. A user, e.g., user 140, may, for instance, utilize the client device 106 to interact with one or more servers, or other components of system 100. The camera 120 may capture still or video images of the user 140, e.g., a video of the face of the user 140. The camera 120 may be integrated with the client device 106 (e.g., smartphone camera) or may be a standalone camera (e.g., webcam or other such camera) that is connected to the client device 106.

A component of system 100 may communicate with one or more components of system 100 via a communication network 150 (e.g., Internet, a mobile phone network, a mobile voice or data network, a cable network, a public switched telephone network, or other types of communications network or combinations of communications networks). The communication network 150 may be a wireless or wired network. As an example, the client device 106 and the computer system 102 may communicate wirelessly.

It should be noted that, while one or more operations are described herein as being performed by particular components of computer system 102, those operations may, in some embodiments, be performed by other components of computer system 102 or other components of system 100. As an example, while one or more operations are described herein as being performed by components of computer system 102, those operations may, in some embodiments, be performed by components of client device 106.

It should be noted that, although some embodiments are described herein with respect to machine learning models, other prediction models (e.g., statistical models or other analytics models) may be used in lieu of or in addition to machine learning models in other embodiments (e.g., a statistical model replacing a machine learning model and a non-statistical model replacing a non-machine-learning model in one or more embodiments).

In some embodiments, system 100 facilitates determination of oculometric parameters 170-178 of a user 140 at a high resolution (e.g., sub-pixel level, 0.1 mm or higher resolution) using a video stream 125 (e.g., a sequence of frames of an image of the eye) of the eye movements captured by the camera 120. The video management subsystem 112 obtains the video stream 125 from the client device 106 and stores the video stream 125 in the database 132. The OPS 114 processes the video stream 125 to extract the oculometric parameters, such as (i) pupil center 176, (ii) pupil radius 178, (iii) iris radius 174, (iv) iris translation 172, and (v) iris rotation 170 of each of the eyes, among other parameters, at a high resolution. These oculometric parameters may be used to determine eye movement parameters (e.g., pupillary response parameters and gaze parameters) that are indicative of eye movements responsive to a non-standard stimuli (e.g., a video or image displayed on the client device 106). The marker subsystem 116 may produce digital biomarkers (e.g., parameters) based on the eye movement parameters that may act as an indicator of one or more neurological disorders.

The video management subsystem 112 may store the video stream 125 in the database 132 in any of several formats (e.g., WebM, Windows Media Video, Flash Video, AVI, QuickTime, AAC, MPEG-4, or another file format). The video management subsystem 112 may also provide the video stream 125 as an input (e.g., in real-time) to the OPS 114 for generating the oculometric parameters. In some embodiments, the video management subsystem 112 may perform preprocessing 191 of the video stream 125 to convert the video stream 125 to a format that is suitable for oculometric parameter extraction by the OPS 114. For example, the video management subsystem 112 may perform an extract, transform and load (ETL) process on the video stream 125 to generate a preprocessed video stream 151 for the OPS 114. The ETL process is typically a multi-phase process where data is first extracted then transformed (e.g., cleaned, sanitized, scrubbed) and finally loaded into a target system. The data may be collated from one or more sources, and it may also be outputted to one or more destinations. In one example, the ETL process performed by the video management subsystem 112 may include adjusting color and brightness (e.g., white balance) in the video stream 125. In another example, the ETL process may include reducing noise from the video stream 125. In yet another example, the ETL process may include improving resolution of the video stream 125 based on multi-frame data, for example, by implementing one or more multi-frame super-resolution techniques that recover a high-resolution image (or a sequence) from a sequence of low-resolution images. In some embodiments, super-resolution is a digital image processing technique to obtain a single high-resolution image (or a sequence) from multiple blurred low-resolution images. The basic idea of super-resolution is that the low-resolution images of the same scene contain different information because of relative subpixel shifts; thus, a high-resolution image with higher spatial information can be reconstructed by image fusion. The video management subsystem 112 may perform the above preprocessing operations and other such similar preprocessing operations to generate a preprocessed video stream 151 that is of a format suitable for the OPS 114 to perform the oculometric parameter extraction.

In some embodiments, the video management subsystem 112 may obtain the preprocessed video stream 151 via a prediction model (e.g., based on the video stream 125 obtained from the client device 106). As an example, the video management subsystem 112 may input the video stream 125 obtained from the client device 106 to the prediction model, which then outputs the preprocessed video stream 151. In some embodiments, the system 100 may train or configure a prediction model to facilitate the generation of a preprocessed video stream. In some embodiments, system 100 may obtain a video stream from a client device associated with a user (e.g., video stream 125 having a video of a face of the user 140) and provide such information as input to a prediction model to generate predictions (e.g., preprocessed video stream 151 in which color or brightness are adjusted, resolution of the video is improved, etc.). System 100 may provide reference feedback to the prediction model and the prediction model may update one or more portions of the prediction model based on the predictions and the reference feedback. As an example, where the prediction model generates predictions based on video stream obtained from a client device, one or more preprocessed video streams associated with such input video streams may be provided as reference feedback to the prediction model. As an example, a particular preprocessed video stream may be verified as a suitable video stream for oculometric parameter extraction by the OPS 114 (e.g., via user confirmation of the preprocessed video, via one or more subsequent actions demonstrating such goal, etc.) based on one or more user responses or one or more other user actions via one or more services. The foregoing user input information may be provided as input to the prediction model to cause the prediction model to generate predictions of the preprocessed video stream, and the verified preprocessed video stream may be provided as reference feedback to the prediction model to update the prediction model. In this way, for example, the prediction model may be trained or configured to generate more accurate predictions. In some embodiments, the training dataset may include several data items in which each data item includes at least a video obtained from a client device and a corresponding preprocessed video as the ground truth.

In some embodiments, the foregoing operations for updating the prediction model may be performed with a training dataset with respect to one or more users (e.g., a training dataset associated with a given user to specifically train or configure the prediction model for the given user, a training dataset associated with a given cluster, demographic, or other group to specifically train or configure the prediction model for the given group, a training dataset associated with any given set of users, or other training dataset). As such, in some embodiments, subsequent to the updating of the prediction model, system 100 may use the prediction model to facilitate generation of a preprocessed video stream for facilitating oculometric parameter extraction by the OPS 114.

The video management subsystem 112 may generate the preprocessed video stream 151 prior to inputting the video stream 125 to the OPS 114, or after storing the video stream 125 in the database 132. Further, the video management subsystem 112 may also store the preprocessed video stream 151 in the database 132 along with the video stream 125.

The OPS 114 may process the video stream 125 or the preprocessed video stream 151 to extract, determine, derive, or generate the oculometric parameters (e.g., oculometric parameters 170-178), which are characteristic of the eyes 145 of the user 140. In some embodiments, the oculometric parameters include parameters such as (i) a pupil center 176, (ii) a pupil radius 178, (iii) an iris radius 174, (iv) an iris translation 172, and (v) an iris rotation 170. The pupil center 176 is a center of the pupil and may be represented using coordinates (e.g., three-dimensional (3D) lateral displacement vector (x,y,z)) that identifies a location of the pupil center in a coordinate system. The pupil radius 178 may be a radius of the pupil and may be represented as a scalar with distance units. The iris translation 172 (or iris translation 160) is a center of the iris and may be represented using coordinates (e.g., 3D lateral displacement vector (x,y,z)) that identify a location of the iris center in a coordinate system. The iris radius 174 (or iris radius 162) may be a radius of the iris and may be represented as a scalar with distance units. In some embodiments, the iris radius 174 is assumed to have a small variance in the human population (e.g., 10%-15% considering iris radius varies from 11 mm-13 mm among the human population). The iris rotation 170 (or iris rotation 158) is representative of a rotation of the iris and is retrieved as the iris normal vector (e.g., perpendicular to the iris circle plain). In some embodiments, the iris rotation 170 may be projected to a 3D vector in a device coordinate system (e.g., x, y, z) or represented by a 2D vector in a head coordinate system (e.g., azimuth angle and elevation angle). In some embodiments, the OPS 114 may obtain the coordinates of the oculometric parameters in one or more coordinate systems, such as the device coordinate system or the head coordinate system illustrated in FIGS. 3A and 3B, respectively.

Figure 3A:
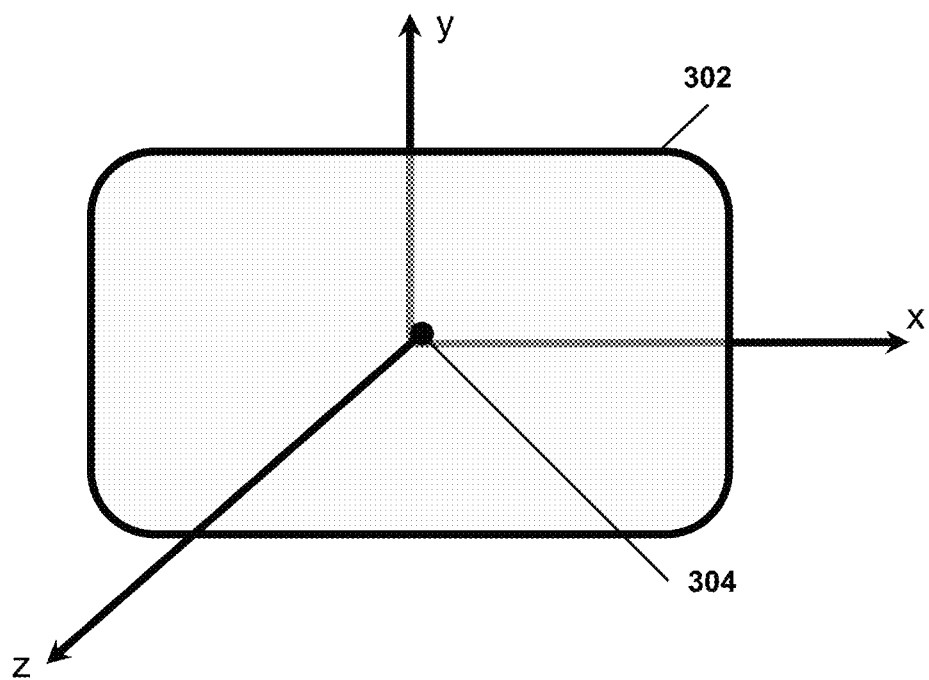
FIG. 3A illustrates a device coordinate system, consistent with various embodiments.

FIG. 3A illustrates a device coordinate system, consistent with various embodiments. In some embodiments, the device coordinate system is a cartesian coordinate system, with a center of a display 302 of a client device (e.g., the client device 106) considered as an origin 304 having the (x,y,z) coordinates as (0,0,0). The device coordinate system defines the three orthogonal axes, e.g., x-axis in the direction of the horizontal edge of the display 302, y-axis in the direction of the vertical edge of the display 302 and perpendicular to the x-axis, and z-axis in a direction perpendicular to the plane of the display 302.

Figure 3B:
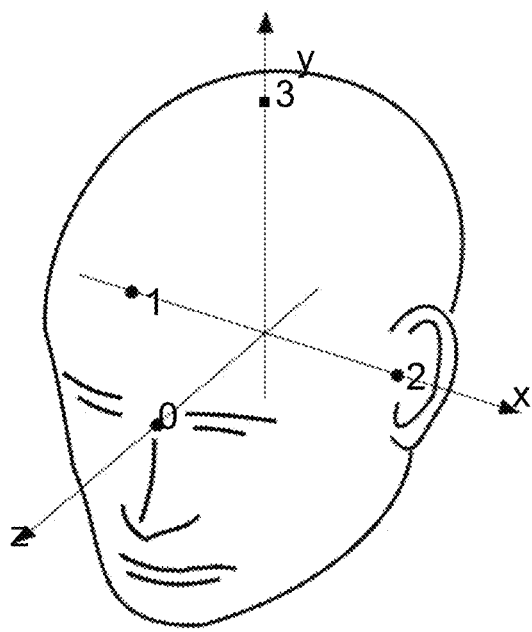
FIG. 3B illustrates a head coordinate system, consistent with various embodiments.

FIG. 3B illustrates a head coordinate system, consistent with various embodiments. In some embodiments, the head coordinate system is defined by a plane that contains the following points in the face bounding polygon: most left, most right and most upper (points 1, 2 and 3 in FIG. 3B) detectable points in the face polygon. For example, the upper most point 3 may be defined as the most upper detectable point in the face bounding polygon and may be located in the cross-section between the y-axis and the head. When obtaining a face image, it is The horizontal axis (x) may be defined as the line between the most left and the most right points, and the perpendicular vector to that line on the defining plane may be defined as the vertical axis (y). The depth axis (2) may be orthogonal to both the x and y axes. The origin of the head coordinate system (point 0 in the FIG. 3B) is located in the center between the eyes, as projected on the defining plane by displacement on the z-direction. In some embodiments, the iris rotation may be represented on the head coordinate system as the eyeball rotation, given two angles (e.g., azimuth and elevation).

Referring to the OPS 114, the OPS 114 may be configured to represent the coordinates of the oculometric parameters in any of the coordinate systems, including the head coordinate system or the device coordinate system. Further, the OPS 114 may be configured to convert the coordinates from one coordinate system to another, such as from the head coordinate system to the device coordinate system or vice versa.

The OPS 114 may also obtain eyelid data 164, such as coordinates of the upper eyelid boundary and lower eyelid boundary of both the eyes. The eyelid data 164 may be used in determining, or in improving the accuracy of, the oculometric parameters. In some embodiments, the OPS 114 may obtain the above data (e.g., oculometric parameters 170-178, eyelid data 164 or other data) as time series data. For example, the OPS 114 may extract a first set of values of the oculometric parameters 170-178 for a first moment in time of the video stream 125, a second set of values of the oculometric parameters 170-178 for a second moment in time of the video stream 125 and so on. That is, the OPS 114 may continuously extract the oculometric parameters 170-178 at a specified time interval (e.g., every millisecond, every few milliseconds, or other temporal resolution). Further, the OPS 114 may obtain the above data for one or both the eyes 145 of the user 140.

The OPS 114 may perform several processes to extract the above oculometric parameters (e.g., oculometric parameters 170-178) from the preprocessed video stream 151. For example, in an extraction process 192, the OPS 114 may obtain a first set of oculometric parameters, such as iris data 153, eyelid data 155 and pupil center 157. In some embodiments, the OPS 114 may use computer vision techniques on the preprocessed video stream 151 to model the translation and rotation of a face of the user 140 with respect to the camera 120 and to identify the eyes and the mouth in the face. After identifying the position of the eyes, the OPS 114 may obtain the eyelid data 155 (e.g., coordinates of an array of points that describe a polygon representing the eye lids) for each frame (e.g., using the fact that their edge may be approximated with quadratic functions). In some embodiments, the OPS 114 may determine the iris data 153 (e.g., a shape, such as an ellipsoid, representing the iris) by determining the pixels that are in or out of the iris radius at any moment in time based on the eyelid's location as a time series. In some embodiments, the OPS 114 may be configured to consider that the iris and pupil are ellipsoids with a relatively uniform and dark color compared to the sclera (e.g., the white part of the eye) in determining the pixels that are in or out. The iris data 153 may include several coordinates such as a first coordinate and a second coordinate, which correspond to right and left coordinates of a shape representing the iris (e.g., an ellipse); a third coordinate and fourth coordinate, which correspond to top and bottom coordinates of the shape; and a fifth coordinate corresponding to a center of the iris. The pupil center 157 may also be determined based on the time series of the eyelid data 155 and iris data 153. In some embodiments, the pupil center 157 may include a coordinate representing a location of the center of the pupil.

In some embodiments, the OPS 114 may implement a prediction model in the extraction process 192 and may obtain the first set of oculometric parameters via the prediction model (e.g., based on the video stream 125 or the preprocessed video stream 151). As an example, the OPS 114 may input the video stream 125 or the preprocessed video stream 151 to the prediction model, which then outputs the first set of oculometric parameters. In some embodiments, the system 100 may train or configure a prediction model to facilitate the generation of the first set of oculometric parameters. In some embodiments, system 100 may obtain a video stream having a video of the face of a user (e.g., video stream 125 or preprocessed video stream 151) and provide such information as input to a prediction model to generate predictions (e.g., first set of oculometric parameters such as iris data, eyelid data, pupil center, etc.). System 100 may provide reference feedback to the prediction model and the prediction model may update one or more portions of the prediction model based on the predictions and the reference feedback. As an example, where the prediction model generates predictions based on the video stream 125 or the preprocessed video stream 151, the first of oculometric parameters associated with such input video streams may be provided as reference feedback to the prediction model. As an example, a particular set of oculometric parameters may be verified as an appropriate set of oculometric parameters (e.g., via user confirmation of the set of oculometric parameters, via one or more subsequent actions demonstrating such goal, etc.). The foregoing user input information may be provided as input to the prediction model to cause the prediction model to generate predictions of the first set of oculometric parameters, and the verified set of oculometric parameters may be provided as reference feedback to the prediction model to update the prediction model. In this way, for example, the prediction model may be trained or configured to generate more accurate predictions.

In some embodiments, the foregoing operations for updating the prediction model may be performed with a training dataset with respect to one or more users (e.g., a training dataset associated with a given user to specifically train or configure the prediction model for the given user, a training dataset associated with a given cluster, demographic, or other group to specifically train or configure the prediction model for the given group, a training dataset associated with any given set of users, or other training dataset). As such, in some embodiments, subsequent to the updating of the prediction model, system 100 may use the prediction model to facilitate generation of a first set of oculometric parameters.

In some embodiments, the OPS 114 may also further adjust, modify, or correct the first set of parameters based on other factors, such as optometric data associated with a user. For example, the user 140 may have certain vision conditions such as myopia, hyperopia, astigmatism or other vision conditions and the user may wear corrective lenses such as eyeglasses or contact lens. The OPS 114 may consider such optometric conditions of the user 140 and correct, adjust or modify, values of one or more of the first set of oculometric parameters. In some embodiments, the OPS 114 may obtain the optometric data associated with the user 140 from user profile data (e.g., stored in the database 132).

In some embodiments, the OPS 114 may further process 193 the iris data 153 to extract iris related parameters such as iris rotation 158, iris translation 160 and iris radius 162. In some embodiments, the above iris related parameters are obtained using an ML technique. For example, the OPS 114 may implement a maximum likelihood estimation (MLE) based curve fitting method to estimate the iris related parameters. The iris data is provided as input to the MLE-based curve fitting method (e.g., oval fit-based on an assumption that iris is circular and so when projected to a 2D plane it is oval/ellipse), which generates the above iris related parameters. In some embodiments, in statistics, MLE is a method of estimating the parameters of a probability distribution by maximizing a likelihood function, so that under the assumed statistical model the observed data is most probable. The point in the parameter space that maximizes the likelihood function is called the maximum likelihood estimate. In some embodiments, curve fitting operation is a process of constructing a curve, or mathematical function, that has the best fit to a series of data points, subject to constraints (e.g., oval fit). Curve fitting may involve either interpolation, where an exact fit to the data is required, or smoothing, in which a "smooth" function is constructed that approximately fits the data. Fitted curves may be used as an aid for data visualization, to infer values of a function where no data are available, and to summarize the relationships among two or more variables.

In some embodiments, by performing the MLE-based curve fitting operation the accuracy of at least some of the iris related parameters may be further improved. For example, the shape depicting the iris boundary is further improved from the coordinates of the shape in the iris data 153, and therefore an improved or more accurate iris radius 162 may be determined. In some embodiments, the iris translation 160, also referred to as iris center, is similar to the coordinates of the iris center in the iris data 153. In some embodiments, in the process 193, the OPS 114 may consider different iris centers, construct an iris shape for each of the candidate iris centers, and assign a confidence score for each of the shapes. Such a method may be repeated for different iris centers, and the shape having a score satisfying a score criterion (e.g., the best score) is selected. In some embodiments, the score for each iteration may reflect a log-likelihood of the examined parameter set (e.g., coordinates of the iris shape, radius and center), based on the known physical constraints and assumptions. In some embodiments, the physical constraints and assumptions may improve the efficiency of the MLE process by introducing better estimated initial conditions before iterating towards convergence. For example, some assumptions may include that: the iris is circular (which when projected on a plane as 2D is represented as ellipse/oval, iris center is expected at the centroid of the circles, high contrast between iris and sclera, degree of similarity of orientation between left and right eye, stimulus-based assumption on the expected gaze point, and brightness of a display of the client device on which a video stimulus is shown to the user. In some embodiments, examples of physical constraints may include: pupil dilation dependence in overall brightness (light conditions), limited range of face orientation as users look at the display, blinking may initiate uncertainty due to readjustment time, or physical possible range of motion (both face and eyeball).

The OPS 114 may perform a deconvolution process 194 on the video stream 125 or the preprocessed video stream 151 to adjust (e.g., improve the resolution or increase the accuracy of) some oculometric parameters, such as the eyelid data 155 and pupil center 166, and determine other oculometric parameters, such as the pupil radius. In some embodiments, the OPS 114 may perform a blind deconvolution process to improve the accuracy of the oculometric parameters. In image processing, blind deconvolution is a deconvolution technique that permits recovery of the target scene from a single or a set of "blurred" images in the presence of a poorly determined or unknown point spread function (PSF). Regular linear and non-linear deconvolution techniques may utilize a known PSF. For blind deconvolution, the PSF is estimated from the image or image set, allowing the deconvolution to be performed. Blind deconvolution may be performed iteratively, whereby each iteration improves the estimation of the PSF and the scene, or non-iteratively, where one application of the algorithm, based on exterior information, extracts the PSF. After determining the PSF, the PSF may be used in deconvolving the video stream 125 or the preprocessed video stream 151 to obtain the adjusted oculometric parameters (e.g., adjusted eyelid data 164, adjusted pupil center 166 or pupil radius 168).

In some embodiments, applying blind deconvolution algorithm may help in decreasing or removing the blurring in the images/video, and in estimating irradiance (e.g., based on parameters of the deduced convolution vector (e.g., PSF)). In some embodiments, the estimated irradiance is an estimated irradiance reflected from the eye of the user 140, which is an indication of the irradiance the eyes are exposed to. After the blurring is reduced or removed and the irradiance is obtained, the deconvolution process may be repeated one or more times to obtain adjusted oculometric parameters (e.g., whose accuracy or resolution is improved compared to oculometric parameters prior to the deconvolution process 194).

In some embodiments, in determining the PSF, the blind deconvolution process considers various factors. For example, the OPS 114 may input (a) the video stream 125 or the preprocessed video stream 151 (e.g., which is a time-series image sequence) with high temporal resolution (e.g., equal to or faster than 30 ms per frame); (b) stimulus data such as spatio-temporal information on a stimulus presented on the display of the client device 106, and optical properties information on the of the stimulus, including spectral properties (e.g., color) and intensity (e.g., brightness); (c) environment data such as lighting in the environment (e.g., a room) where the user is located, which can be measured using information obtained from the camera 120, (d) device data such as orientation information of the client device 106, information from one or more sensors associated with the client device 106 such as acceleration sensors. Such factors help in efficient calculation of the PSF, minimizes the noise uncertainty, leading to better accuracy in the overall deconvolution.

In some embodiments, the deconvolution process 194 is integrated with an MLE process to further improve the accuracy of the oculometric parameters. For example, the MLE process may be used to improve the accuracy of the eyelid data 155. As described above, the eyelid data 155 includes coordinates of an array of points that describe a shape (e.g., polygon) of the eyelids. The MLE process performs a parabolic curve fitting operation on the eyelid data 155 with a constraint that the eyelids are parabolic in shape to obtain a more accurate representation of the eyelids, as the adjusted eyelid data 164. In some embodiments, the adjusted eyelid data 164 may include coordinates of a collection of points that describe a shape (e.g., parabolic) of an eyelid. Such adjusted eyelid data 164 may be obtained for both eyelids of the eye and for both eyes. In some embodiments, the OPS 114 may use the adjusted eyelid data 164 information to predict the precise oculometric parameter values, such as the pupil radius center, even when some are physically challenging (e.g., when the upper eyelid covers the pupil center, or when only some of the iris is exposed to the camera.

In some embodiments, the MLE process may also be used for obtaining or improving pupil related data, such as pupil radius 168. In some embodiments, by performing the MLE-based curve fitting operation the accuracy of the pupil related data may be further improved. In some embodiments, in the MLE process, the OPS 114 may consider different pupil centers, construct a pupil shape for each of the candidate pupil centers, and assign a confidence score for each of the shapes. Such a method may be repeated for different pupil centers, and the shape having a score satisfying a score criterion (e.g., the best score) is selected. Once the shape is selected, the corresponding center is selected as the adjusted pupil center 166 and the pupil radius 168 may be determined based on the selected shape and the adjusted pupil center 166. In some embodiments, the score for each iteration may reflect a log-likelihood of the examined parameter set (e.g., pupil radius and center), based on the known physical constraints and assumptions. In some embodiments, the physical constraints and assumptions may improve the efficiency of the MLE process by introducing better estimated initial conditions before iterating towards convergence. For example, some assumptions may include that: the pupil is circular (which when projected on a 2D plane is represented as ellipse/oval, pupil center is expected at the centroid of the circle, degree of similarity of orientation between left and right eye, stimulus-based assumption on the expected gaze point, and brightness of a display of the client device on which a video stimulus is shown to the user. In some embodiments, examples of physical constraints may include: pupil dilation dependence in overall brightness (light conditions), limited range of face orientation as users look at the display, blinking may initiate uncertainty due to readjustment time, or physical possible range of motion (both face and eyeball). Accordingly, the OPS 114 may obtain adjusted oculometric parameters, such as the adjusted eyelid data 164, adjusted pupil center 166 and the pupil radius 168 from the deconvolution process 194. In some embodiments, the above process 193 of processing iris data and the deconvolution process 194 may output the following oculometric parameters-adjusted eyelid data 164, adjusted pupil center 166 and the pupil radius 168, the iris rotation 158, iris translation 160 and iris radius 162 (also referred to as "a first set of oculometric parameters") in a first resolution. For example, the first resolution may be at a pixel level or other lower resolution.

In some embodiments, the OPS 114 may further improve the resolution of the first set of oculometric parameters. For example, the OPS 114 may improve the resolution from the first resolution to a second resolution (e.g., 0.1 mm, sub-pixel level or some other resolution that is greater than the first resolution). In some embodiments, the OPS 114 may input the first set of oculometric parameters to an improve resolution process 195 to obtain a second set of oculometric parameters (e.g., oculometric parameters 170-178) at the second resolution. In some embodiments, the improve resolution process 195 may obtain the second set of oculometric parameters via a prediction model (e.g., based on the first set of oculometric parameters). As an example, the OPS 114 may input the first set of oculometric parameters obtained at the first resolution to the prediction model, which then outputs the second set of oculometric parameters at the second resolution. In some embodiments, the system 100 may train or configure a prediction model to facilitate the generation of the second set of oculometric parameters. In some embodiments, system 100 may obtain input data such as (a) a video stream having a video of the face of a user (e.g., video stream 125 or preprocessed video stream 151), (b) the first set of oculometric parameters (obtained at a first resolution as described above), (c) environment data such as lighting in the environment (e.g., a room) where the user is located, which can be measured using information obtained from the camera 120, (d) device data such as a display size, display resolution, display brightness, or display contrast associated with a display of the client device 106, model and manufacturer information of the camera 120, or (e) user information such as demographic, clinical history, optometric data, etc.

The system 100 may provide such input data to a prediction model to generate predictions (e.g., the second set of oculometric parameters such as iris rotation 170, iris translation 172, iris radius 174, pupil center 176, and pupil radius 178 at a second resolution). System 100 may provide reference feedback to the prediction model and the prediction model may update one or more portions of the prediction model based on the predictions and the reference feedback. As an example, where the prediction model generates predictions based on the above input data, a second set of oculometric parameters associated with such input data may be provided as reference feedback to the prediction model. As an example, a particular set of oculometric parameters obtained at the second resolution may be verified as an appropriate set of oculometric parameters (e.g., via user confirmation of the set of oculometric parameters, via one or more subsequent actions demonstrating such goal, etc.). The foregoing user input information may be provided as input to the prediction model to cause the prediction model to generate predictions of the second set of oculometric parameters, and the verified set of oculometric parameters may be provided as reference feedback to the prediction model to update the prediction model. In this way, for example, the prediction model may be trained or configured to generate more accurate predictions. In some embodiments, the reference feedback having the oculometric parameters at the second resolution may be obtained, determined or derived from information obtained using any of several eye tracking devices that produce oculometric parameters at a high resolution (e.g., the second resolution). For example, some tracking devices produce oculometric parameters such as gaze origin, gaze point and pupil diameter at the second resolution. The OPS 114 may derive the second set of oculometric parameters such as the iris rotation, iris translation, iris radius, pupil center, and pupil radius from the oculometric parameters generated using the eye tracking device and provide the derived second set of oculometric parameters as reference feedback to train the prediction model. Such reference feedback may be obtained for several videos and provided as training dataset to train the prediction model.

In some embodiments, the foregoing operations for updating the prediction model may be performed with a training dataset with respect to one or more users (e.g., a training dataset associated with a given user to specifically train or configure the prediction model for the given user, a training dataset associated with a given cluster, demographic, or other group to specifically train or configure the prediction model for the given group, a training dataset associated with any given set of users, or other training dataset). As such, in some embodiments, subsequent to the updating of the prediction model, system 100 may use the prediction model to facilitate generation of a first set of oculometric parameters.

In some embodiments, the OPS 114 may also extract additional oculometric parameters such as a pupil visible fraction, a pupil coverage asymmetry, iris visible fraction, or iris coverage asymmetry. In some embodiments, the pupil visible fraction is calculated as the ratio between the pupil area not covered by the eyelids and the pupil iris area. The pupil coverage asymmetry may be defined as the mean of the pupil upper eyelid covered fraction and the pupil lower eyelid covered fraction when the upper eyelid covered fraction is represented in a positive value, and the lower eyelid covered fraction is represented in a negative value, normalized by the iris total covered area. The values of this parameter may vary between −1 and 1 and project the asymmetry between the eyelid coverage of the upper and the lower eyelids (e.g., "−1" may denote that all covered area is covered by the lower eyelid, "1" may denote that all covered area is covered by the upper eyelid, and "0" may denote that the upper and lower eyelids cover equal areas).

The OPS 114 may extract the additional oculometric parameters based on the second set of oculometric parameters 170-178. For example, the OPS 114 may perform geometrical projections and calculations using the second set of oculometric parameters 170-178 to determine the additional oculometric parameters.

In some embodiments, the OPS 114 may also extract, generate or derive the eye movement parameters (e.g., pupillary response parameters and gaze parameters) that are indicative of eye movements responsive to a non-standard stimulus (e.g., a video or image displayed on the client device 106). The eye movement parameters may be derived using the second set of oculometric parameters (e.g., obtained as described above). In some embodiments, the pupillary response parameter is indicative of a response of the eye to a particular stimulus, and the gaze parameters are indicative of where the eyes are focused or looking. The OPS 114 may obtain different types of gaze parameters, such as fixation, saccade, pursuit, or another gaze parameter. In some embodiments, fixation is defined as the distribution of eye movements while inspecting a specific area of the stimulus. In some embodiments, saccade is defined as the distribution of eye movements between inspection areas. In some embodiments, pursuit is defined as the distribution of eye movements while following movement. These eye movement parameters may be used in generating various digital biomarkers.

In some embodiments, the marker subsystem 116 may produce digital biomarkers (e.g., parameters) that may act as an indicator of one or more neurological disorders. The marker subsystem 116 may produce the digital biomarkers based on based on the oculometric parameters or the eye movement parameters (e.g., discussed above). In some embodiments, these digital biomarkers are tightly correlated (and can therefore serve as proxies) for disease progression or acuity. The digital biomarkers generated by the marker subsystem 116 may be objective, sensitive, accurate (0.1 mm or less), or correlated with clinical progression of diseases, and may be obtained remotely, outside of lab settings and even in a distributed manner.

Note that the oculometric parameters, the eye movement parameters, or the digital biomarkers may be obtained in real-time (e.g., based on a real-time video stream obtained from the camera 120) or offline (e.g., using a video stored in the database 132). Further, the oculometric parameters (e.g., second set of oculometric parameters 170-178 or other oculometric parameters) are obtained as time-series data and for one or more eyes of the user. That is, the oculometric parameters 170-178 may be extracted continuously at a specified time interval (e.g., every millisecond, every few milliseconds, or other temporal resolution).

In some embodiments, the prediction models described above may include one or more neural networks or other machine learning models. As an example, neural networks may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections can be enforcing or inhibitory in their effect on the activation state of connected neural units. In some embodiments, each individual neural unit may have a summation function which combines the values of all its inputs together. In some embodiments, each connection (or the neural unit itself) may have a threshold function such that the signal must surpass the threshold before it propagates to other neural units. These neural network systems may be self-learning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free-flowing, with connections interacting in a more chaotic and complex fashion.

A neural network may be trained (i.e., whose parameters are determined) using a set of training data (e.g., ground truths). The training data may include a set of training samples. Each sample may be a pair comprising an input object (typically an image, a measurement, a tensor or vector which may be called a feature tensor or vector) and a desired output value (also called the supervisory signal). A training algorithm analyzes the training data and adjusts the behavior of the neural network by adjusting the parameters (e.g., weights of one or more layers) of the neural network based on the training data. For example, given a set of N training samples of the form $\{(x_1, y_1), (x_2, y_2), \ldots (x_N, y_N)\}$ such that $x_i$ is the feature tensor/vector of the i-th example and $y_i$ is its supervisory signal, a training algorithm seeks a neural network g: $X \rightarrow Y$, where X is the input space and Y is the output space. A feature tensor/vector is an n-dimensional tensor/vector of numerical features that represent some object (e.g., a complex electric field image). The tensor/vector space associated with these vectors is often called the feature or latent space. After training, the neural network may be used for making predictions using new samples.

Figure 2:
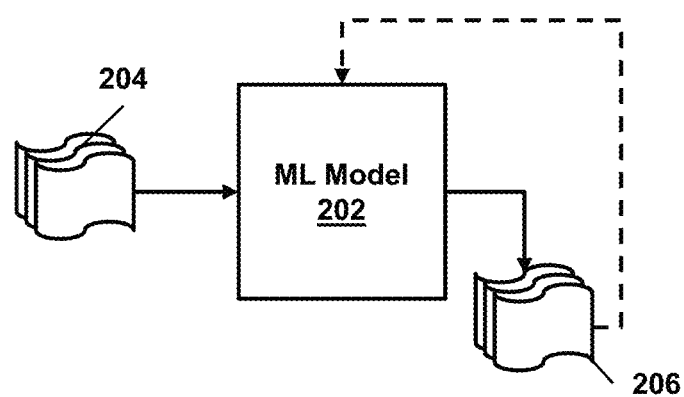
FIG. 2 shows a machine learning model configured to facilitate prediction of oculometric parameters, in accordance with one or more embodiments.

As an example, with respect to FIG. 2, machine learning model 202 may take inputs 204 and provide outputs 206. In one use case, outputs 206 may be fed back to machine learning model 202 as input to train machine learning model 202 (e.g., alone or in conjunction with user indications of the accuracy of outputs 206, labels associated with the inputs, or with other reference feedback information). In another use case, machine learning model 202 may update its configurations (e.g., weights, biases, or other parameters) based on its assessment of its prediction (e.g., outputs 206) and reference feedback information (e.g., user indication of accuracy, reference labels, or other information). In another use case, where machine learning model 202 is a neural network, connection weights may be adjusted to reconcile differences between the neural network's prediction and the reference feedback. In a further use case, one or more neurons (or nodes) of the neural network may require that their respective errors are sent backward through the neural network to them to facilitate the update process (e.g., backpropagation of error). Updates to the connection weights may, for example, be reflective of the magnitude of error propagated backward after a forward pass has been completed. In this way, for example, the machine learning model 202 may be trained to generate better predictions.

Figure 4:
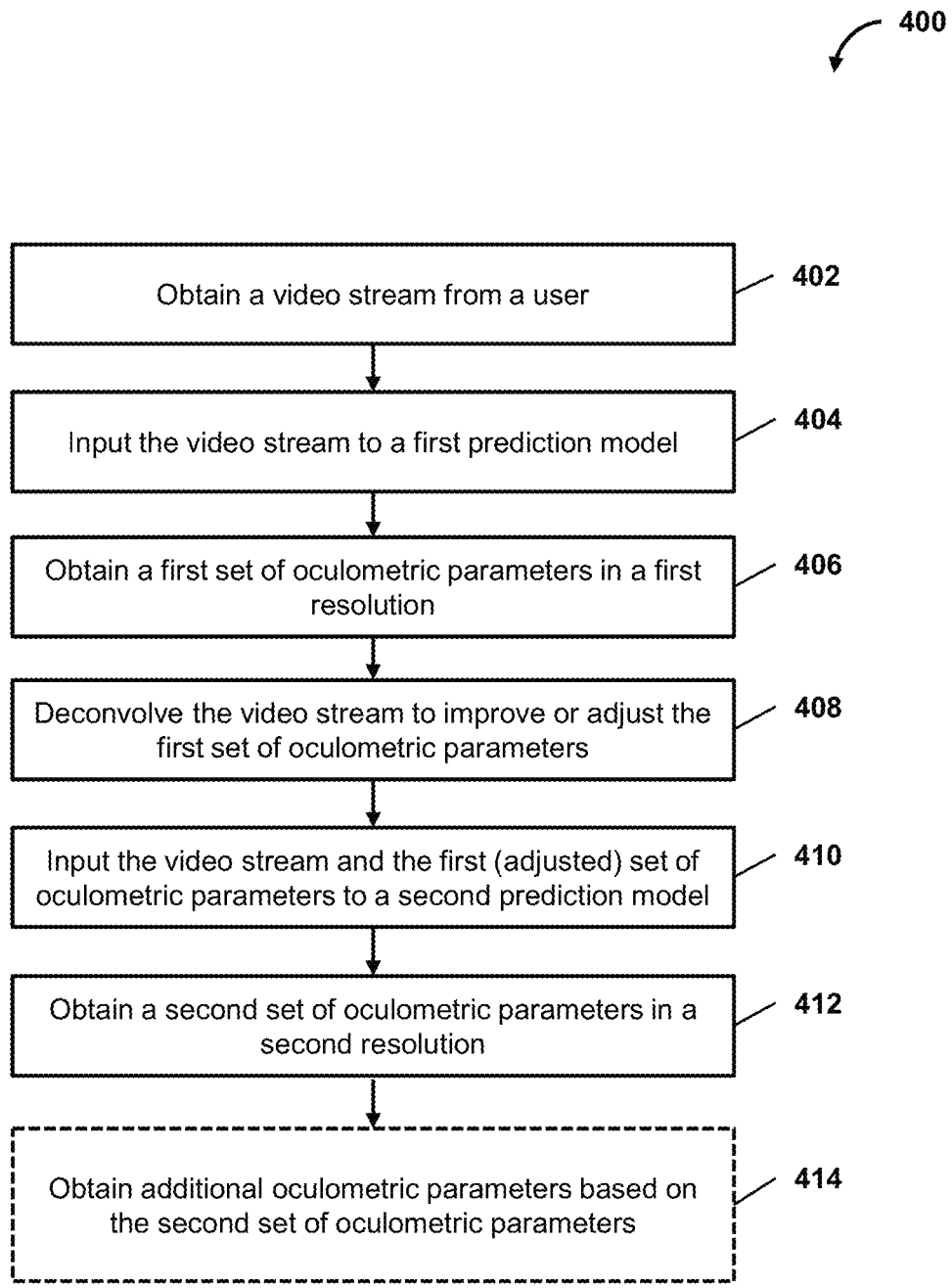
FIG. 4 is a flow diagram of a process for obtaining oculometric parameters at a high resolution, consistent with various embodiments.

FIG. 4 is a flow diagram of a process 400 for obtaining oculometric parameters at a high resolution, consistent with various embodiments. In some embodiments, the process 400 may be executed in the system 100 of FIG. 1A.

In an operation 402, a video stream is obtained from a client device associated with a user. The video stream may include a video of a face of the user. For example, the video stream 125 is obtained from the client device 106. In some embodiments, the video stream may be obtained in real-time from the client device, e.g., capture by a camera associated with the client device such as the camera 120 of the client device 106, or may be a recorded video that is obtained from a data storage device, e.g., database 132, data storage or a memory on the client device, or other data storage devices.

In an operation 404, the video stream is input to a first prediction model to obtain a first set of oculometric parameters. In some embodiments, the video stream may be pre-processed prior to being input to the first prediction model. In some embodiments, preprocessing the video stream may include performing an ETL process on the video stream to adjust color and brightness (e.g., white balance) in the video stream, reduce noise from the video stream, improve resolution of the video stream by implementing one or more multi-frame super-resolution techniques, or other such video processing. For example, the video stream input to the first prediction model may be the video stream 125 or the preprocessed video stream 151.

In an operation 406, the first set of oculometric parameters are obtained from the first prediction model. The oculometric parameters correspond to various characteristics of an eye. For example, the first set of oculometric parameters may include iris data, eyelid data and pupil center. The iris data may include coordinates of several points that describe a center and a shape (e.g., an ellipse) of the iris. The eyelid data may include coordinates of an array of points that describe a shape (e.g., a polygon) representing the eyelids. The pupil center may include a coordinate of a point representing the center of the pupil. In some embodiments, the first set of oculometric parameters are obtained at a first resolution. For example, the first resolution may be at a pixel level or other lower resolution. In some embodiments, the iris data is further processed to obtain iris rotation, iris translation and iris radius from the iris data. For example, the iris data 153 is processed to obtain the iris rotation 158, iris translation 160 and iris radius 162. The iris rotation may be representative of a rotation of the iris and may be retrieved as the iris normal vector (e.g., perpendicular to the iris circle plain). The iris translation may be a center of the iris and may be represented using coordinates that identify a location of the iris center. The iris radius may be a radius of the iris and may be represented as a scalar with distance units. In some embodiments, an MLE-based curve fitting method may be performed to estimate the iris related parameters. The iris data is provided as input to the MLE-based curve fitting method (e.g., oval fit), which generates the above iris related parameters.

In an operation 408, the video stream is deconvolved to adjust (e.g., improve accuracy or resolution) the first set of oculometric parameters. The video stream input to the deconvolution process may be the video stream 125 or the preprocessed video stream 151. In some embodiments, the video stream is deconvolved by using a blind deconvolution process integrated with an MLE process, the additional details of which are described above at least with reference to FIGS. 1A and 1B and below at least with reference to FIG. 5. In some embodiments, applying blind deconvolution algorithm may help in decreasing or removing the blurring in the images/video, or any other noise from the video stream to improve the accuracy of the oculometric parameters extracted. The deconvolution process may be repeated one or more times to obtain the adjusted oculometric parameters (e.g., whose accuracy or resolution is improved compared to the oculometric parameters prior to the deconvolution process). The adjusted parameters may include adjusted eyelid data, adjusted pupil center and pupil radius.

In an operation 410, the video stream and the first set of parameters are input to a second prediction model to obtain the oculometric parameters at a high resolution. For example, the first set of oculometric parameters, including the iris rotation 158, iris translation 160, the iris radius 162, the adjusted eyelid data 164, adjusted pupil center 166 and pupil radius 168, etc. are input to the second prediction model. In some embodiments, the second prediction model is trained to predict the set of oculometric parameters at a high resolution. For example, the second prediction model is trained with several training datasets in which each dataset includes a video of the face of the user, device data of the client device, environment data of an environment in which the user is located and user information of the user as input data, and the corresponding set of oculometric parameters at a high resolution as the ground truth. In some embodiments, the set of oculometric parameters at the high resolution is obtained using one or more eye tracking devices that are configured to produce the oculometric parameters at a high resolution.

In an operation 412, a second set of oculometric parameters are obtained at a second resolution from the second prediction model. For example, the second set of oculometric parameters including iris rotation 170, iris translation 172, iris radius 174, pupil center 176, and pupil radius 178 are obtained at a second resolution (e.g., 0.1 mm, sub-pixel level or some other resolution greater than the first resolution).

Optionally, in an operation 414, additional set of oculometric parameters may be obtained. For example, additional oculometric parameters such as a pupil visible fraction, a pupil coverage asymmetry, iris visible fraction, or iris coverage asymmetry may be obtained based on the second set of oculometric parameters. The OPS 114 may obtain the addition oculometric parameters by performing geometrical projections and calculations using the second set of oculometric parameters. In some embodiments, the pupil visible fraction is calculated as the ratio between the pupil area not covered by the eyelids and the pupil iris area. The pupil coverage asymmetry may be defined as the mean of the pupil upper eyelid covered fraction and the pupil lower eyelid covered fraction when the upper eyelid covered fraction is represented in a positive value, and the lower eyelid covered fraction is represented in a negative value, normalized by the iris total covered area. The values of this parameter may vary between −1 and 1 and project the asymmetry between the eyelid coverage of the upper and the lower eyelids (e.g., "−1" may denote that all covered area is covered by the lower eyelid, "1" may denote that all covered area is covered by the upper eyelid, and "0" may denote that the upper and lower eyelids cover equal areas.

Operations 402-414 may be performed by a subsystem that is the same as or similar to OPS 114, in accordance with one or more embodiments.

Figure 5:
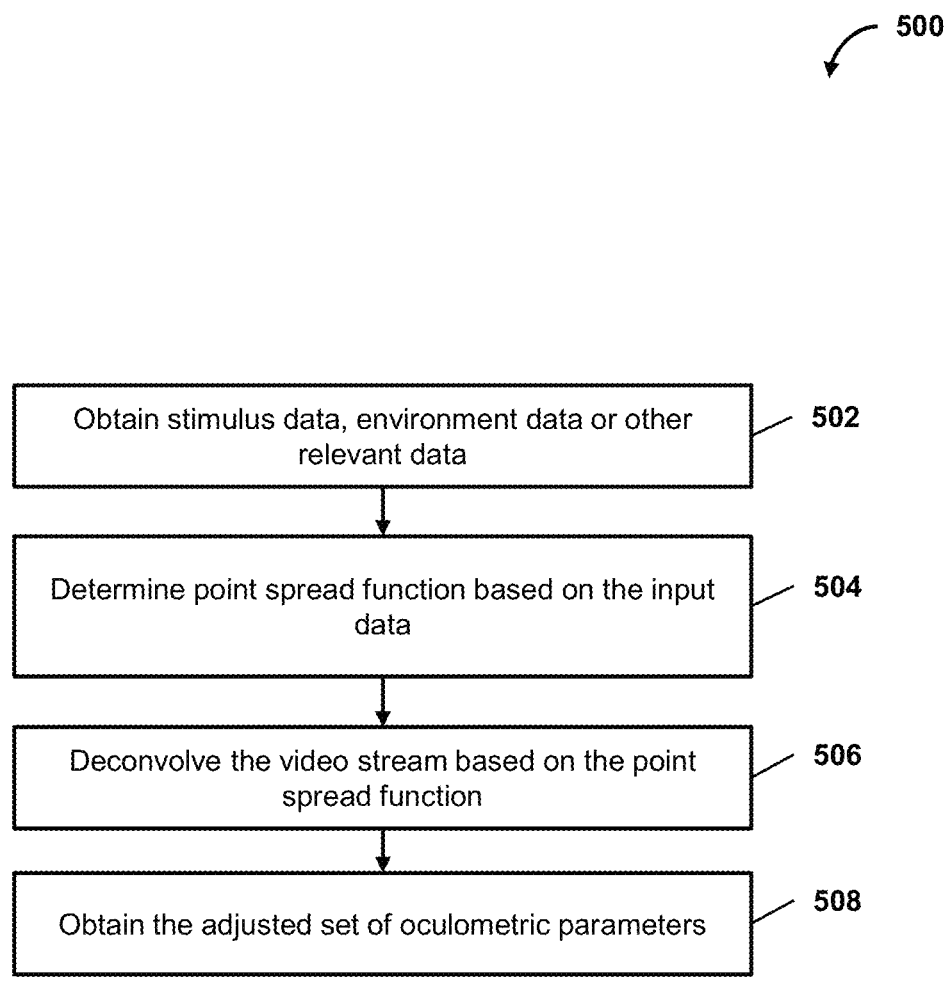
FIG. 5 is a flow diagram of a process for deconvolving a video stream to obtain adjusted oculometric parameters, consistent with various embodiments.

FIG. 5 is a flow diagram of a process 500 for deconvolving a video stream to obtain adjusted oculometric parameters, consistent with various embodiments. In some embodiments, the process 500 may be performed as part of operation 408 of process 400.

In an operation 502, input data such as the video stream, stimulus data, environment data, device data or other data is obtained to perform deconvolution of the video stream. The video stream input to the deconvolution process may be the video stream 125 or the preprocessed video stream 151. The stimulus data may include spatio-temporal information on a stimulus presented on the display of the client device 106, or optical properties information on the of the stimulus, including spectral properties (e.g., color) and intensity (e.g., brightness). The environment data may include information such as lighting in the environment (e.g., a room) in which the user is located, which can be measured using information obtained from the camera 120. The device data may include information such as orientation information of the client device 106, information from one or more sensors associated with the client device 106 such as acceleration sensors. Further, the input data may also include eyelid data (e.g., eyelid data 155) and the pupil center (e.g., pupil center 157).

In an operation 504, a point spread function of the blind deconvolution algorithm is determined based on the input data.

In an operation 506, the video stream is deconvolved based on the point spread function. The deconvolution process removes or reduces any blurring, or any other noise introduced into the video stream due to user environment related factors, client device related factors, camera related factors, video stimulus related factors etc. to improve the video stream and therefore, improve the accuracy of the oculometric parameters retrieved.

In an operation 508, the adjusted oculometric parameters are derived from the deconvolved video stream as described above. For example, the adjusted oculometric parameters may include adjusted eyelid data 164, adjusted pupil center 166 or pupil radius 168. In some embodiments, the deconvolution process is integrated with an MLE process to further improve the accuracy of the oculometric parameters. For example, the MLE process may be used to improve the accuracy of the eyelid data 155. The MLE process may be used to perform a parabolic curve fitting operation on the eyelid data 155 to obtain a more accurate representation of the eyelids, as adjusted eyelid data 164. In another example, the MLE process may be used to obtain or improve the accuracy of pupil related data, such as pupil radius 168. The MLE process may be used to perform a curve fitting operation (e.g., oval fit) to improve a shape of the pupil. For example, the MLE process may consider different pupil centers, and may construct a pupil shape for each of the candidate pupil centers and assign a confidence score for each of the shapes. Such a method may be repeated for different pupil centers, and the shape having a score satisfying a score criterion (e.g., the best score) is selected. Once the shape is selected, the corresponding center may be selected as the adjusted pupil center 166 and the pupil radius 168 may be determined based on the selected shape and the adjusted pupil center 166.

In some embodiments, the process 500 may be repeated one or more times (e.g., until the accuracy or resolution of the oculometric parameters satisfy a criterion (e.g., exceed a threshold value) or the PSF satisfies a criterion) to improve the accuracy or resolution of the adjusted oculometric parameters.

In some embodiments, the various computers and subsystems illustrated in FIG. 1A may include one or more computing devices that are programmed to perform the functions described herein. The computing devices may include one or more electronic storages (e.g., prediction database(s) 132, which may include training data database(s) 134 to store training data, model database(s) 136 to store prediction models, etc., or other electronic storages), one or more physical processors programmed with one or more computer program instructions, and/or other components. The computing devices may include communication lines or ports to enable the exchange of information within a network (e.g., network 150) or other computing platforms via wired or wireless techniques (e.g., Ethernet, fiber optics, coaxial cable, Wi-Fi, Bluetooth, near field communication, or other technologies). The computing devices may include a plurality of hardware, software, and/or firmware components operating together. For example, the computing devices may be implemented by a cloud of computing platforms operating together as the computing devices.

The electronic storages may include non-transitory storage media that electronically stores information. The storage media of the electronic storages may include one or both of (i) system storage that is provided integrally (e.g., substantially non-removable) with servers or client devices or (ii) removable storage that is removably connectable to the servers or client devices via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storage may store software algorithms, information determined by the processors, information obtained from servers, information obtained from client devices, or other information that enables the functionality as described herein.

The processors may be programmed to provide information processing capabilities in the computing devices. As such, the processors may include one or more of a digital processor, an analog processor, a digital circuit designed to process information, an analog circuit designed to process information, a state machine, and/or other mechanisms for electronically processing information. In some embodiments, the processors may include a plurality of processing units. These processing units may be physically located within the same device, or the processors may represent processing functionality of a plurality of devices operating in coordination. The processors may be programmed to execute computer program instructions to perform functions described herein of subsystems 112-116 or other subsystems. The processors may be programmed to execute computer program instructions by software; hardware; firmware; some combination of software, hardware, or firmware; and/or other mechanisms for configuring processing capabilities on the processors.

It should be appreciated that the description of the functionality provided by the different subsystems 112-116 described herein is for illustrative purposes, and is not intended to be limiting, as any of subsystems 112-116 may provide more or less functionality than is described. For example, one or more of subsystems 112-116 may be eliminated, and some or all of its functionality may be provided by other ones of subsystems 112-116. As another example, additional subsystems may be programmed to perform some or all of the functionality attributed herein to one of subsystems 112-116.

Figure 6:
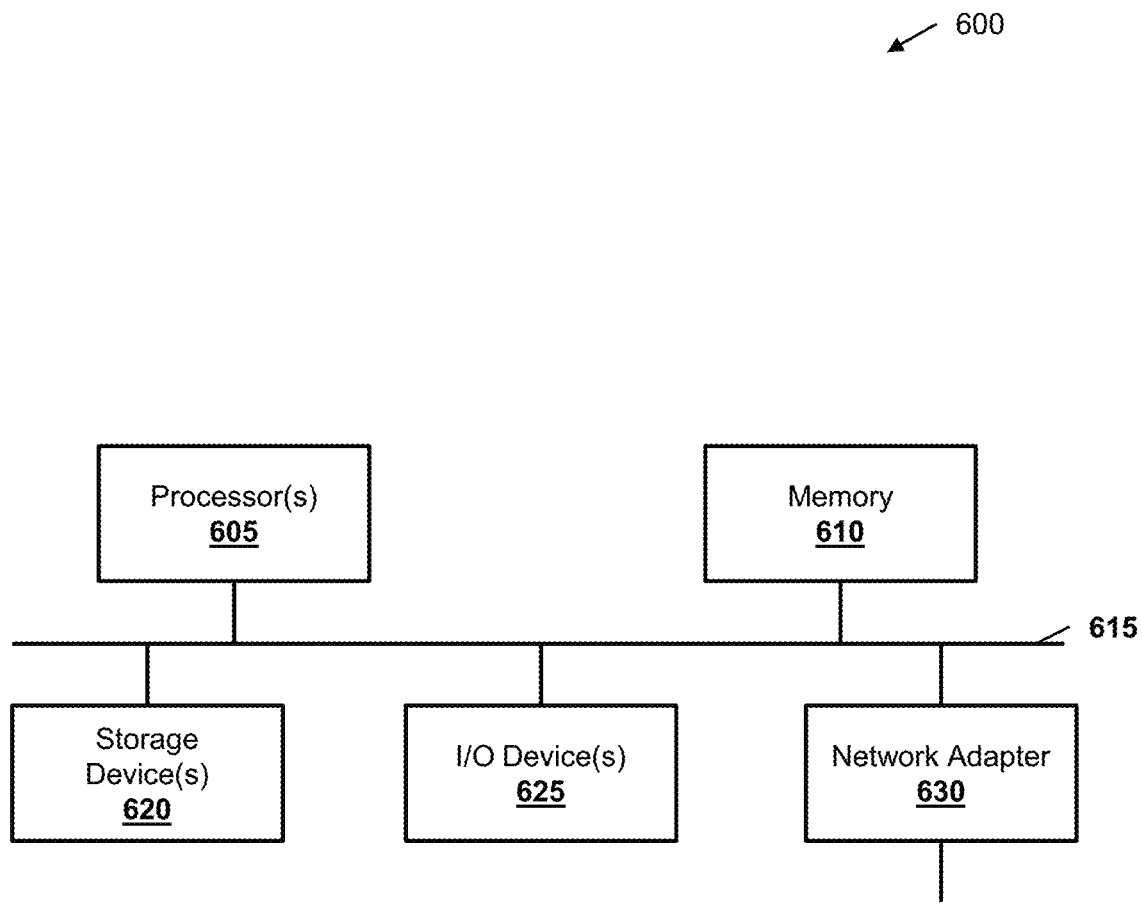
FIG. 6 is a block diagram of a computer system as may be used to implement features of the disclosed embodiments.

FIG. 6 is a block diagram of a computer system as may be used to implement features of the disclosed embodiments. The computer system 600 may be used to implement any of the entities, subsystems, components or services depicted in the examples of the foregoing figures (and any other components described in this specification). The computer system 600 may include one or more central processing units ("processors") 605, memory 610, input/output devices 625 (e.g., keyboard and pointing devices, display devices), storage devices 620 (e.g., disk drives), and network adapters 630 (e.g., network interfaces) that are connected to an interconnect 615. The interconnect 615 is illustrated as an abstraction that represents any one or more separate physical buses, point to point connections, or both connected by appropriate bridges, adapters, or controllers. The interconnect 615, therefore, may include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Components (IEEE) standard 1394 bus, also called "Firewire".

The memory 610 and storage devices 620 are computer-readable storage media that may store instructions that implement at least portions of the described embodiments. In addition, the data structures and message structures may be stored or transmitted via a data transmission medium, such as a signal on a communications link. Various communications links may be used, such as the Internet, a local area network, a wide area network, or a point-to-point dial-up connection. Thus, computer readable media can include computer-readable storage media (e.g., "non-transitory" media) and computer-readable transmission media. The storage media of the electronic storages may include one or both of (i) system storage that is provided integrally (e.g., substantially non-removable) with servers or client devices or (ii) removable storage that is removably connectable to the servers or client devices via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storage may store software algorithms, information determined by the processors, information obtained from servers, information obtained from client devices, or other information that enables the functionality as described herein.

The instructions stored in memory 610 can be implemented as software and/or firmware to program the processor(s) 605 to carry out actions described above. The processors may be programmed to execute computer program instructions by software; hardware; firmware; some combination of software, hardware, or firmware; and/or other mechanisms for configuring processing capabilities on the processors. In some embodiments, such software or firmware may be initially provided to the computer system 600 by downloading it from a remote system through the computer system 600 (e.g., via network adapter 630).

The embodiments introduced herein can be implemented by, for example, programmable circuitry (e.g., one or more microprocessors) programmed with software and/or firmware, or entirely in special-purpose hardwired (non-programmable) circuitry, or in a combination of such forms. Special-purpose hardwired circuitry may be in the form of, for example, one or more ASICs, PLDs, FPGAs, etc.

REMARKS

The above description and drawings are illustrative and are not to be construed as limiting. Numerous specific details are described to provide a thorough understanding of the disclosure. However, in some instances, well-known details are not described in order to avoid obscuring the description. Further, various modifications may be made without deviating from the scope of the embodiments. Accordingly, the embodiments are not limited except as by the appended claims.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. Terms that are used to describe the disclosure are discussed below, or elsewhere in the specification, to provide additional guidance to the practitioner regarding the description of the disclosure. For convenience, some terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms may on occasion be used interchangeably.

Consequently, alternative language and synonyms may be used for any one or more of the terms discussed herein, nor is any special significance to be placed upon whether or not a term is elaborated or discussed herein. Synonyms for some terms are provided. A recital of one or more synonyms does not exclude the use of other synonyms. The use of examples anywhere in this specification including examples of any term discussed herein is illustrative only, and is not intended to further limit the scope and meaning of the disclosure or of any exemplified term. Likewise, the disclosure is not limited to various embodiments given in this specification.

Those skilled in the art will appreciate that the logic illustrated in each of the flow diagrams discussed above, may be altered in various ways. For example, the order of the logic may be rearranged, substeps may be performed in parallel, illustrated logic may be omitted; other logic may be included, etc.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions will control.

Although the present invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the scope of the appended claims. For example, it is to be understood that the present invention contemplates that, to the extent possible, one or more features of any embodiment can be combined with one or more features of any other embodiment.

What is claimed is:

1. A method comprising:
    obtaining a video stream from a client device associated with a user, the video stream including a video of a face of the user;
    providing as input the video stream to a first prediction model to obtain a first set of oculometric parameters of an eye of the user, the first set of oculometric parameters including first iris data or first eyelid data, wherein the first set of oculometric parameters are obtained at a first resolution;
    deconvolving the video stream based on the first eyelid data, stimulus data, or environment data to obtain adjusted eyelid data as part of the first set of oculometric parameters, the stimulus data including spatio-temporal information or optical information of a video stimulus presented on a display associated with the client device, the environment data including light conditions in an environment the client device is in; and providing as input the first set of oculometric parameters to a second prediction model to obtain a second set of oculometric parameters at a second resolution, wherein the second set of oculometric parameters includes second iris data including an iris radius, an iris translation, or an iris rotation, and wherein the second resolution is greater than the first resolution.

2. The method of claim 1, wherein the first resolution is measured in terms of a pixel or other lower resolution value and the second resolution is measured in terms of a sub-pixel value.

3. The method of claim 1, wherein providing the input to the second prediction model includes:

training the second prediction model using a plurality of datasets to predict the second set of oculometric parameters at the second resolution, wherein each dataset includes a video of a face of a specified user, a first set of values corresponding to the first set of oculometric parameters obtained at the first resolution, and a set of labels having a second set of values corresponding to the second set of oculometric parameters obtained at the second resolution.

4. The method of claim 3, wherein the second set of values corresponding to the second set of oculometric parameters is obtained using an eye-tracking device that is configured to obtain the second set of oculometric parameters at the second resolution for a video of the face of the specified user.

5. The method of claim 1, wherein deconvolving the video stream includes:

determining a point spread function of a deconvolution process based on the first eyelid data, the stimulus data, or the environment data; and deconvolving the video stream using the point spread function to obtain the adjusted eyelid data.

6. The method of claim 5, wherein deconvolving the video stream includes determining the adjusted eyelid data based on a maximal likelihood of a prediction of a location of a first pupil center and an eyelid boundary.

7. The method of claim 5, wherein determining the adjusted eyelid data includes:

processing the first eyelid data using a maximal likelihood estimation curve fitting operation to obtain a parabolic fit of an eyelid of the eye, and obtaining a plurality of coordinates along the parabolic fit as the adjusted eyelid data.

8. The method of claim 1, wherein providing the video stream to the first prediction model to obtain the first set of oculometric parameters further includes:

obtaining user data associated with the user, the user data including optometric data of the eye of the user, and applying corrections to the first set of oculometric parameters based on the user data.

9. The method of claim 1 further comprising:

determining an additional set of oculometric parameters based on the second set of oculometric parameters, the additional set of oculometric parameters including at least one of a pupil visible fraction, an iris visible fraction, a pupil coverage asymmetry, or an iris coverage asymmetry.

10. A non-transitory computer-readable medium having instructions that, when executed by a computer, cause the computer to execute a method, the method comprising:

obtaining a video stream from a client device associated with a user, the video stream including a video of a face of the user;

providing as input the video stream to a first prediction model to obtain a first set of oculometric parameters of an eye of the user, the first set of oculometric parameters including first iris data or first eyelid data;

deconvolving the video stream based on the first eyelid data, stimulus data, or environment data to obtain adjusted eyelid data as part of the first set of oculometric parameters, the stimulus data including spatio-temporal information or optical information of a video stimulus presented on a display associated with the client device, the environment data including light conditions in an environment the client device is in; and providing as input the first set of oculometric parameters to a second prediction model to obtain a second set of oculometric parameters at a greater resolution than the first set of oculometric parameters, wherein the second set of oculometric parameters includes an iris radius, an iris translation, or an iris rotation.

11. The computer-readable medium of claim 10, wherein providing the input to the second prediction model includes:

training the second prediction model using a plurality of datasets to predict the second set of oculometric parameters, wherein each dataset includes a video of a face of a specified user, a first set of values corresponding to the first set of oculometric parameters obtained at a specified resolution, and a set of labels having a second set of values corresponding to the second set of oculometric parameters obtained at a resolution greater than the specified resolution.

12. The computer-readable medium of claim 11, wherein the second set of values corresponding to the second set of oculometric parameters is obtained using an eye-tracking device that is configured to obtain the second set of oculometric parameters at a greater resolution than the specified resolution.

13. The computer-readable medium of claim 10, wherein deconvolving the video stream includes:

determining a point spread function of a deconvolution process based on the first eyelid data the stimulus data or the environment data; and deconvolving the video stream using the point spread function to obtain the adjusted eyelid data.

14. The computer-readable medium of claim 13, wherein deconvolving the video stream includes determining the adjusted eyelid data based on a maximal likelihood of a prediction of a location of a first pupil center and an eyelid boundary.

15. The computer-readable medium of claim 14, wherein determining the adjusted eyelid data includes:

processing the first eyelid data using a maximal likelihood estimation curve fitting operation to obtain a parabolic fit of an eyelid of the eye; and obtaining a plurality of coordinates along the parabolic fit as the adjusted eyelid data.

16. A system, comprising:

one or more memories; and at least one processor each coupled to at least one of the memories and configured to perform operations comprising:

obtaining a video stream from a client device associated with a user, the video stream including a video of a face of the user;

providing as input the video stream to a first prediction model to obtain a first set of oculometric parameters of an eye of the user, the first set of oculometric parameters including first iris data or first eyelid data, wherein the first set of oculometric parameters are obtained at a first resolution;

deconvolving the video stream based on the first eyelid data, stimulus data or environment data to obtain adjusted eyelid data as part of the first set of oculometric parameters, the stimulus data including spatio-temporal information or optical information of a video stimulus presented on a display associated with the client device, the environment data including light conditions in an environment the client device is in; and providing as input the first set of oculometric parameters to a second prediction model to obtain a second set of oculometric parameters at a second resolution, wherein the second set of oculometric parameters includes second iris data including an iris radius, an iris translation, or an iris rotation, and wherein the second resolution is greater than the first resolution.

17. The system of claim 16, wherein the first resolution is measured in terms of a pixel or other lower resolution value and the second resolution is measured in terms of a sub-pixel value.

18. The system of claim 16, wherein providing the input to the second prediction model includes:

training the second prediction model using a plurality of datasets to predict the second set of oculometric parameters at the second resolution, wherein each dataset includes a video of a face of a specified user, a first set of values corresponding to the first set of oculometric parameters obtained at the first resolution, and a set of labels having a second set of values corresponding to the second set of oculometric parameters obtained at the second resolution.

19. The system of claim 18, wherein the second set of values corresponding to the second set of oculometric parameters is obtained using an eye-tracking device that is configured to obtain the second set of oculometric parameters at the second resolution for a video of the face of the specified user.

20. The system of claim 16, wherein deconvolving the video stream includes:

determining a point spread function of a deconvolution process based on the first eyelid data, the stimulus data, or the environment data; and deconvolving the video stream using the point spread function to obtain the adjusted eyelid data.

* * * * *